US 7,419,642 B2

(12) United States Patent
Fowler et al.

(10) Patent No.: US 7,419,642 B2
(45) Date of Patent: Sep. 2, 2008

(54) FLUID DISINFECTION APPARATUS

(75) Inventors: William E. Fowler, Castleton, VT (US); Scott P. Russell, North Clarendon, VT (US); Mark E. Kurtz, Poultney, VT (US)

(73) Assignee: Ultravation, Inc., Poultney, VT (US)

( * ) Notice: Subject to any disclaimer, the term of this patent is extended or adjusted under 35 U.S.C. 154(b) by 615 days.

(21) Appl. No.: 10/508,178

(22) PCT Filed: Nov. 5, 2003

(86) PCT No.: PCT/US03/35446

§ 371 (c)(1),
(2), (4) Date: Sep. 15, 2004

(87) PCT Pub. No.: WO2005/046799

PCT Pub. Date: May 26, 2005

(65) Prior Publication Data

US 2005/0232825 A1    Oct. 20, 2005

Related U.S. Application Data

(63) Continuation-in-part of application No. 10/504,044, filed on Aug. 4, 2004, now abandoned.

(51) Int. Cl.
*A62B 7/08* (2006.01)
(52) U.S. Cl. ...................... 422/121; 250/436
(58) Field of Classification Search ............ 422/121; 250/436
See application file for complete search history.

(56) References Cited

U.S. PATENT DOCUMENTS 3,705,693 A * 12/1972 Franz ..................... 239/600
3,853,227 A * 12/1974 Filipowski ............... 211/162
3,862,409 A *  1/1975 Joella et al. ............... 362/90

(Continued)

FOREIGN PATENT DOCUMENTS

JP    407174401 A    7/1995

(Continued)

OTHER PUBLICATIONS

Steril-Aire Brochure; "Model SE Series UVC Emitters"; Jan. 1999; 6 pages.

(Continued)

*Primary Examiner*—Walter D. Griffin
*Assistant Examiner*—Shanta G Doe
(74) *Attorney, Agent, or Firm*—Kenneth F. Dusyn; Kenneth F. Dusyn & Associates

(57) ABSTRACT

An air disinfection module for use in a HVAC system comprises a first and second housing, each of the housings including at least one support member adjustably coupled with the other to form a framework for varying the lateral distance between the first and second housings. The housings further comprise a lamp assembly that includes at least one ultraviolet radiation source communicating with and projecting from its respective housing towards its opposite housing, and a radiation pervious protective sleeve disposed about the radiation source. Electric transmission means are also included which communicates with the ultraviolet radiation source(s) and with at least one source of electrical power to provide electricity to the ultraviolet radiation sources. At least one cross support member communicating with the protective sleeves and the support members is provided for supporting the sleeves and their corresponding ultraviolet radiation sources between the first and second housings.

35 Claims, 22 Drawing Sheets

U.S. PATENT DOCUMENTS

| | | | |
|---|---|---|---|
| 4,261,350 A * | 4/1981 | Branemark et al. | 606/86 |
| 4,364,495 A * | 12/1982 | Walker | 223/61 |
| 4,461,387 A * | 7/1984 | Belokin, Jr. | 211/85.15 |
| 4,872,980 A | 10/1989 | Maarschalkerweerd | |
| 5,030,125 A * | 7/1991 | Toma et al. | 439/226 |
| 5,219,534 A | 6/1993 | Reynolds | |
| 5,590,390 A * | 12/1996 | Maarschalkerweerd | 422/186.3 |
| 5,660,719 A * | 8/1997 | Kurtz et al. | 210/85 |
| 5,742,063 A | 4/1998 | Scroggins et al. | |
| 5,902,552 A | 5/1999 | Brickley | |
| 6,039,460 A * | 3/2000 | Ng et al. | 362/267 |
| 6,221,314 B1 | 4/2001 | Bigelow | |
| 6,342,188 B1 * | 1/2002 | Pearcey et al. | 422/186.3 |
| 2002/0031460 A1 | 3/2002 | Kulp | |
| 2002/0043504 A1 | 4/2002 | Chen et al. | |
| 2002/0190220 A1 * | 12/2002 | Sarchese et al. | 250/432 R |

OTHER PUBLICATIONS

Steril-Aire Brochure; "Guide To UVC Emitters"; Undated; 6 pages.
Dillard & Salmon; "Coil Cleaning: Myths and Misrepresentations"; Penton Media; 1998; 2 pages.
Scheir & Fencl; "Using UVC Technology To Enhance IAQ"; Heating/Piping/Air Conditioning; Feb. 1996; 6 pages.
Steril-Aire Brochure; "Sterilaire Series Model RSE 2 HO UVC Emitter"; Aug. 1999; 4 pages.
Steril-Aire Brochure; "Sterilight Plus Model RSE 1 SO UVC Emitter"; Jul. 12, 1999; 6 pages.
Steril-Aire Brochure; "X-Mount Plus Model SEN 1 VO UVC Emitter"; Aug. 1999; 6 pages.
Steril-Aire Brochure; "Model DE Series UVC Emitters"; Jan. 1999; 6 pages.
Steril-Aire Brochure; [Untitled]; [Undated]; 4 pages.
Steril-Aire Brochure; Model SA UVSR Stationary Radiometer; Jan. 1999; 3 pages.
Steril-Aire Article; "UV lights save on energy"; Heating/Piping/Air Conditioning; Penton Media, Inc.; Jan. 2000; 2 pages.
Kelly; "Shedding Some Light On IAQ"; RSES Journal; Nov. 1999; 4 pages.
Scarpino et al.; "Ability Of A Fan-Powered UVGI Disinfection Unit To Inactivate Selected Airborne Bacteria"; SOEH Conference; Dec. 1-3, 1994; 4 pages.
Foltz; "Emitters use ultraviolet light to combat airborne bacteria"; The Packer; Oct. 25, 1999; 1 page.
Nye; "A cure for the dreaded 'Dirty Sock Syndrome'?"; The Air Conditioning, Heating and Refrigeration News; Apr. 5, 1999; 2 pages.

* cited by examiner

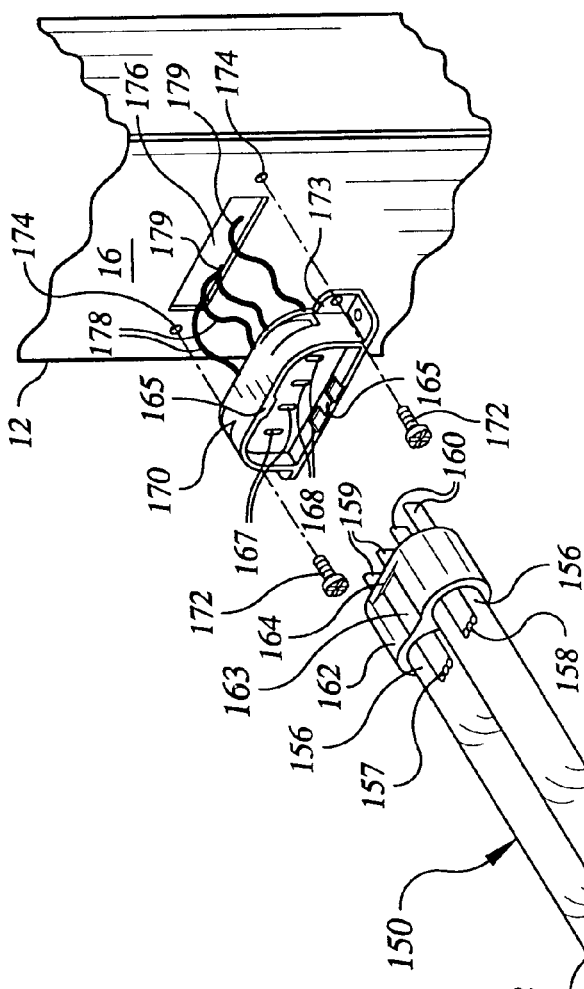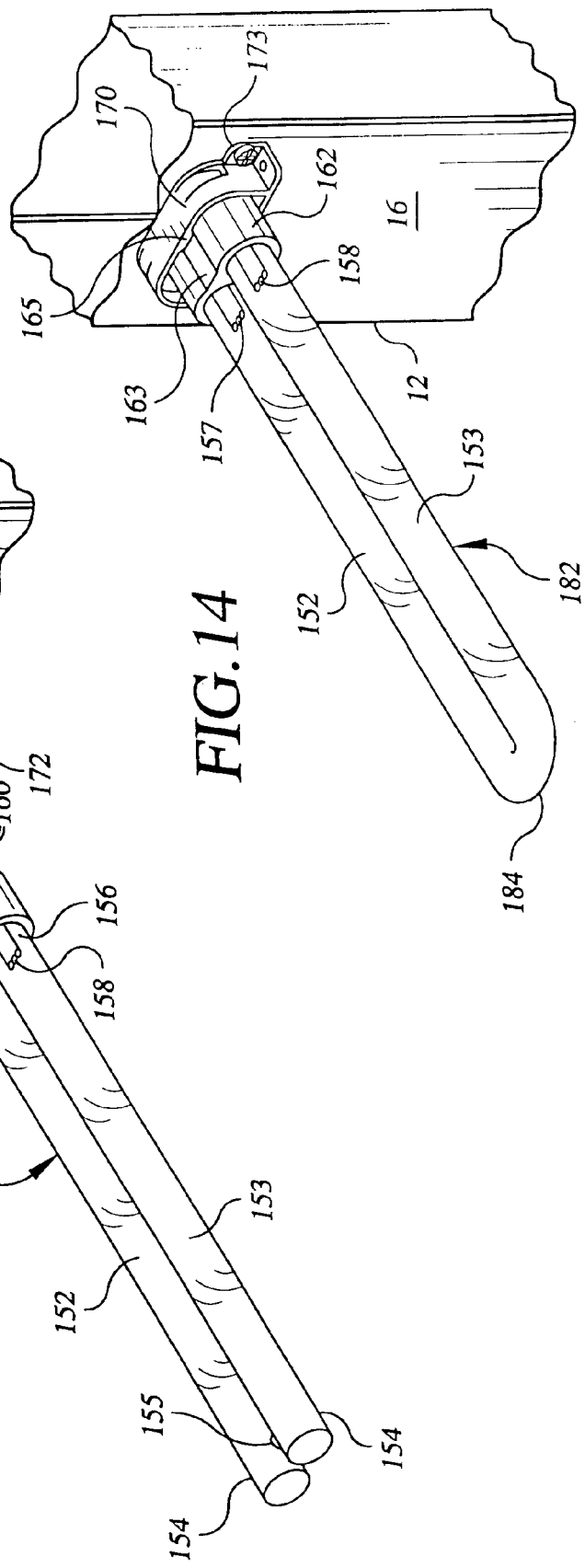

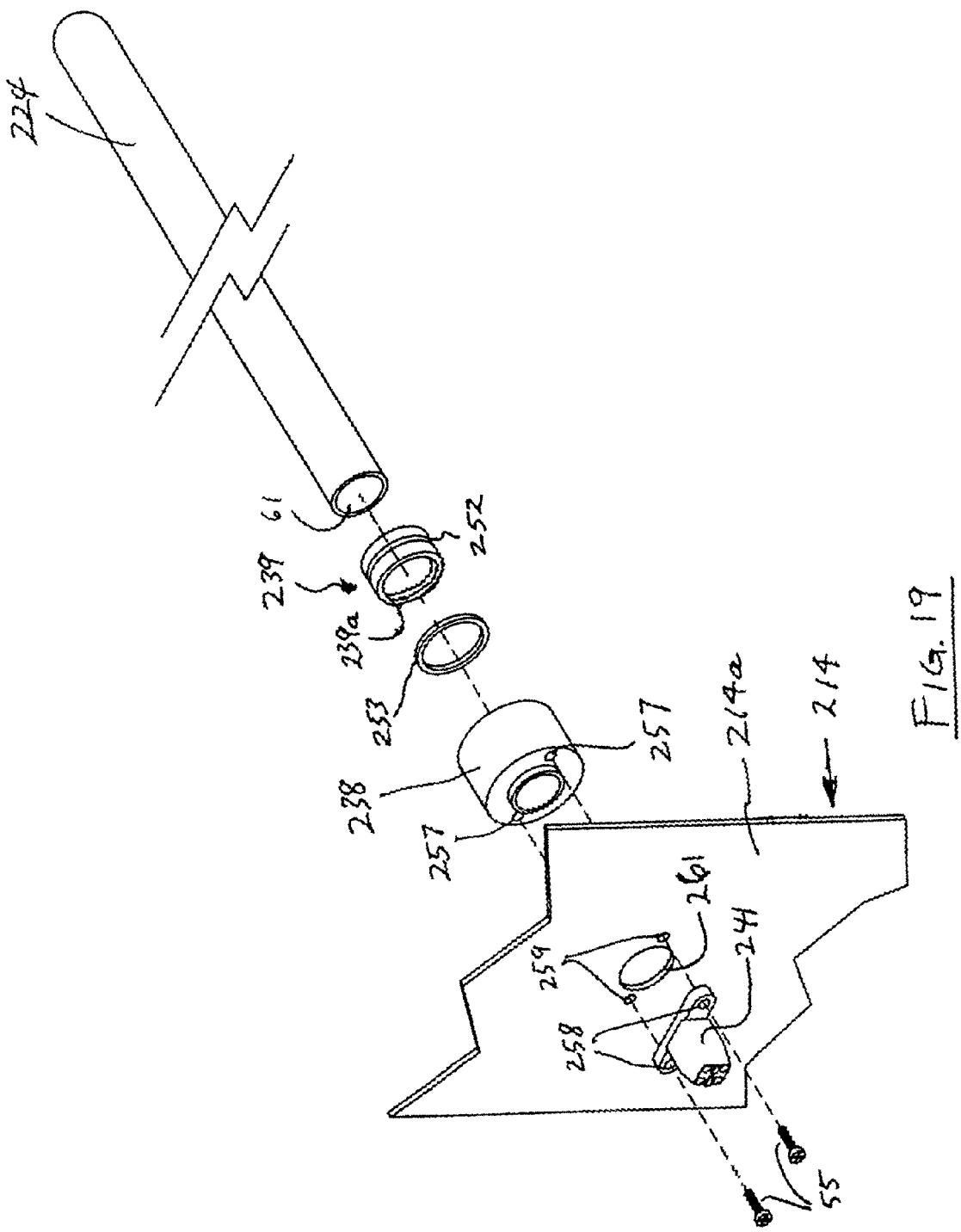

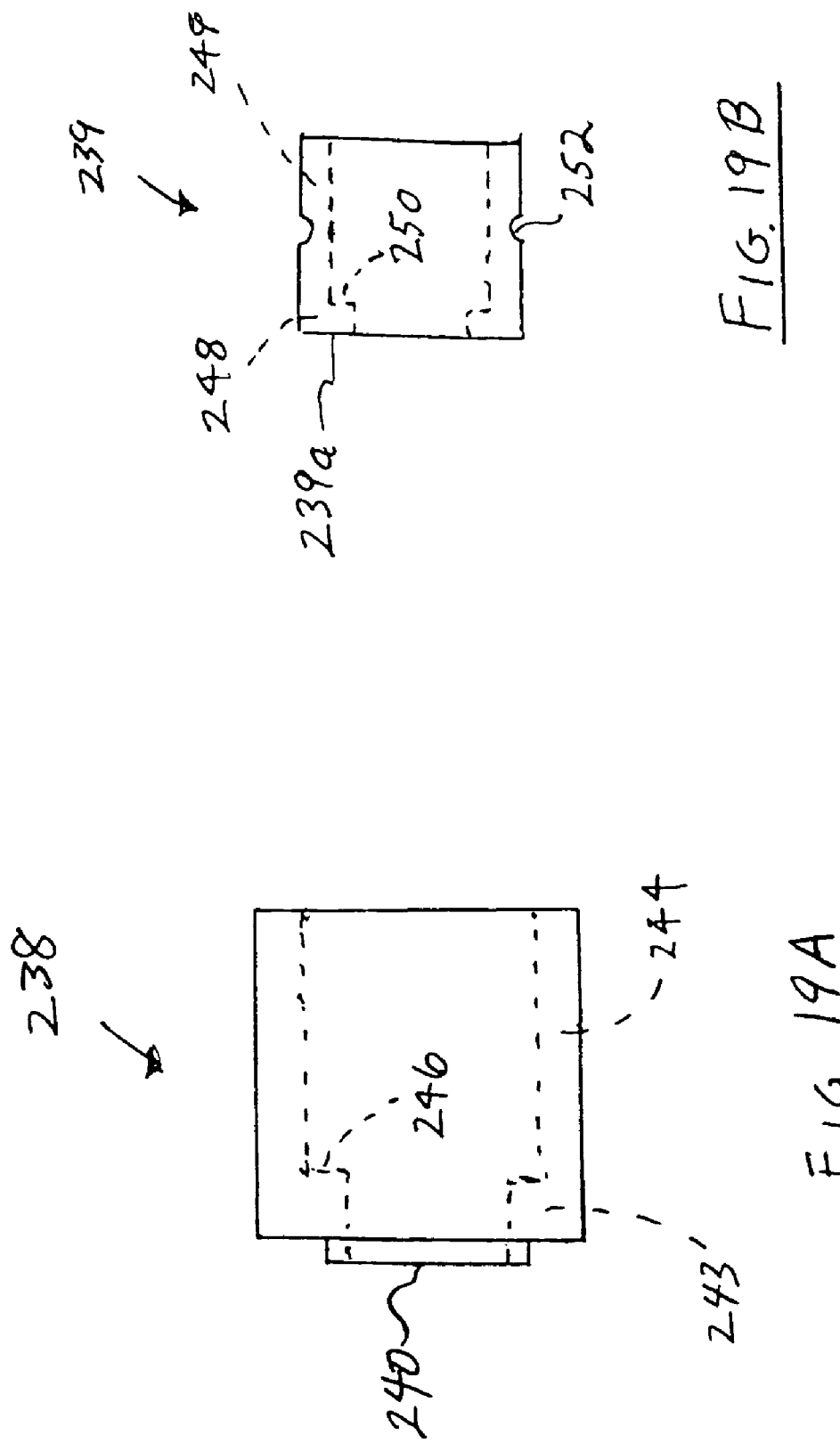

FLUID DISINFECTION APPARATUS

This application is a continuation-in-part of U.S. application Ser. No. 10/504,044 filed Aug. 4, 2004, now abandoned which in turn claims priority to International Application Serial No. PCT/US02/14347 filed 7 May 2002.

BACKGROUND OF THE INVENTION

1. Field of the Invention

The invention broadly relates to a fluid disinfection apparatus utilizing an ultraviolet radiation source. More specifically, the invention provides an air disinfection apparatus and module utilizing a plurality of ultraviolet lamps for incorporation into a heating/ventilation air conditioning ("HVAC") system to disinfect the air passing therethrough.

2. Related Art

U.S. Pat. No. 4,872,980 discloses a plurality of ultraviolet lamps encased in protective quartz sleeves supported at their ends by rigid frame legs. One of the legs is hollow and receives lead wires connected to the lamps through openings spaced along the leg. The opposing leg is provided with receptacles that receive and support the closed ends of the protective sleeves. The lead wires are connected to a ballast located in a frame member connecting the two opposing legs.

U.S. Pat. No. 5,902,552 discloses an ultraviolet air sterilization devices that includes a housing and one or more mounts which connect to germicidal lamp units. Each lamp, which projects into the air stream of an air handling duct, has an integral receptacle with an electrical connection for attachment to a ballast from within the housing.

Arrays or assemblies of lamps having electrical terminal pins carried by lamp bases disposed at each end of the lamp tubings is disclosed in a January, 1999 Steril-Aire, USA, Inc. catalog. The ultraviolet lamps are arranged in a fixed dimensional rack whereby the terminal pins located at each end of the ultraviolet lamps are electrically interfaced with receptacles supported by a side frame. The fixed dimensional rack and multiple assemblies of the rack are designed for installation into a HVAC system in a variety locations, typically in the air-supply side of the duct system, before and/or after the evaporator coils, and/or within the mixed air plenum or return air duct.

SUMMARY OF THE INVENTION

In accordance with the present invention, an air disinfection module is provided for the treatment of a fluid passing through a confined space, more specifically, through a HVAC system. The air disinfection module comprises a first and second housing arranged in laterally spaced-apart relationship to each other by one or more adjustable support members. Each housing includes at least one, preferably a plurality, of lamp assemblies comprising (i) at least one ultraviolet radiation source, typically in the form of an elongate ultraviolet lamp provided with a lamp base disposed at one end thereof and electrical terminal pins mounted to the lamp base, communicating with and projecting from its respective housing towards the opposing housing; and (ii) a radiation pervious protective sleeve, generally of a fused quartz construction, disposed about each radiation source.

The module additionally includes an electric transmission means, preferably in the form of an electrical receptacle, which communicates with the ultraviolet radiation source and with at least one source of electrical power, typically in the form of one or a plurality of ballasts, for supplying electricity to the ultraviolet radiation source.

In order to support the protective sleeves and their corresponding ultraviolet radiation sources between the first and second housings, the module further includes at least one cross support member communicating with the protective sleeves and the adjustable support members. The cross support member comprises retention means communicating with an elongate rigid member, the retention means being configured for detachable securement to the protective sleeves and adjustable support member. The retention means are preferably of a resilient construction in the form of spring clips.

The lamp assemblies are preferably detachably secured to their respective housings by means of an annular lamp assembly receptacle disposed about an opening provided in a wall of the housing from which the ultraviolet lamp(s) projects. The lamp assembly receptacle comprises a first and second annulus, the first annulus being sized and configured for receiving therethrough the lamp base of the ultraviolet lamp. The second annulus is sized and configured with the receptacle's first annulus for defining an interior platform whose function is to limit the slidable penetration within the lamp assembly receptacle of an annular sleeve retention member. The annular sleeve retention member is disposed about, preferably fixed to, the open end of the protective sleeve which overlies the ultraviolet lamp.

As indicated above, the lamp base of the ultraviolet lamp is provided with terminal pins for insertion into the electrical receptacle. The electrical receptacle and lamp assembly receptacle are disposed on opposite sides of the housing wall about the opening that receives the lamp base therethrough, and are secured to each other with fastening means inserted through corresponding openings provided in the electrical receptacle, lamp assembly receptacle and housing wall for that purpose. In this way, the lamp assemblies are enabled to project from their respective housing to the opposing housing.

Each housing of the module generally comprises a plurality of ultraviolet lamp assemblies and a plurality of ballasts for supplying electricity to the ultraviolet lamps.

The support members that connect each of the housings for configuring the module, project from their respective housings and are preferably slidably engaged with each other for varying the lateral distance between the first and second housings. The elongate support members are also preferably disposed about each end of their respective housings and are of a tubular construction, preferably of a cylindrical configuration. In order to secure the attachment of the tubular support member to its respective housing, the support member includes a retaining member which is in the form of a receptacle for receiving a fastening member through an opening provided in a surface of the housing from which the tubular support member projects. The retaining member is preferably configured in the form of a cylindrically shaped bracket structure, generally of an expandable resilient construction, for slidable engagement with the interior of the tubular support member with a resistance fit. For ease of assembly, the receptacle and fastening member are threaded for threaded engagement with each other.

The tubular support members of the first and second housings are slidably engaged in mateable relationship with each other, and are detachably secured to each other by a locking mechanism. The locking mechanism preferably takes the form of a compression fitting.

In order to provide further rigidity to the modular framework and a guide for the slidable engagement of the respective support members with each other, the surface of the tubular support member of the first housing may be provided with a longitudinal and axially disposed channel for slidably receiving a protrusion disposed on the surface of the tubular support member of the second housing. This provides for a mateable engagement of the protrusion and channel when the respective tubular support members are slidably engaged with each other. The channel may be disposed on the interior surface of the tubular support member of the first housing, in which case the protrusion is disposed on the exterior surface of the tubular support member of the second housing. Alternatively, the channel may be disposed on the exterior surface of the tubular support member of the first housing, and in this circumstance, the protrusion will be disposed on the interior surface of the tubular support member of the second housing.

BRIEF DESCRIPTION OF THE DRAWINGS

A complete understanding of the present invention may be obtained by reference to the following specification when taken in conjunction with the accompanying drawings wherein certain preferred embodiments are illustrated and wherein like numerals refer to like parts throughout.

FIG. 13 is an exploded isometric view of detail F illustrated in FIG. 12.

FIG. 14 is an isometric view of another embodiment of the fluid disinfection module illustrated in FIG. 13.

FIG. 19 is an enlarged exploded and fragmentary view of detail A illustrated in FIG. 17.

FIG. 19A is a side elevation of the annular lamp assembly receptacle 238 illustrated in FIG. 19.

FIG. 19B is a side elevation of the annular sleeve retention member 239 illustrated in FIG. 19.

DETAILED DESCRIPTION OF THE INVENTION AND PREFERRED EMBODIMENTS THEREOF

Throughout the following description, the preferred embodiments and examples are intended as exemplars rather than limitations on the apparatus of the present invention.

The present invention provides an apparatus for the germicidal treatment of a fluid, and more specifically to an apparatus that disinfects air passing through a HVAC system utilizing one or more radiation sources. The apparatus described herein has the advantage of being adaptable to the confined spaces within a HVAC system having various cross-sectional dimensions such as those found in commercial and industrial buildings that employ large heating/air conditioning equipment for moving significant volumes of air. The apparatus typically takes the form of a modular structure that employs at least one, generally a plurality, of ultraviolet lamps whose disposition within the HVAC system is configured for maximum exposure to the passage of air therethrough.

Figure 1:
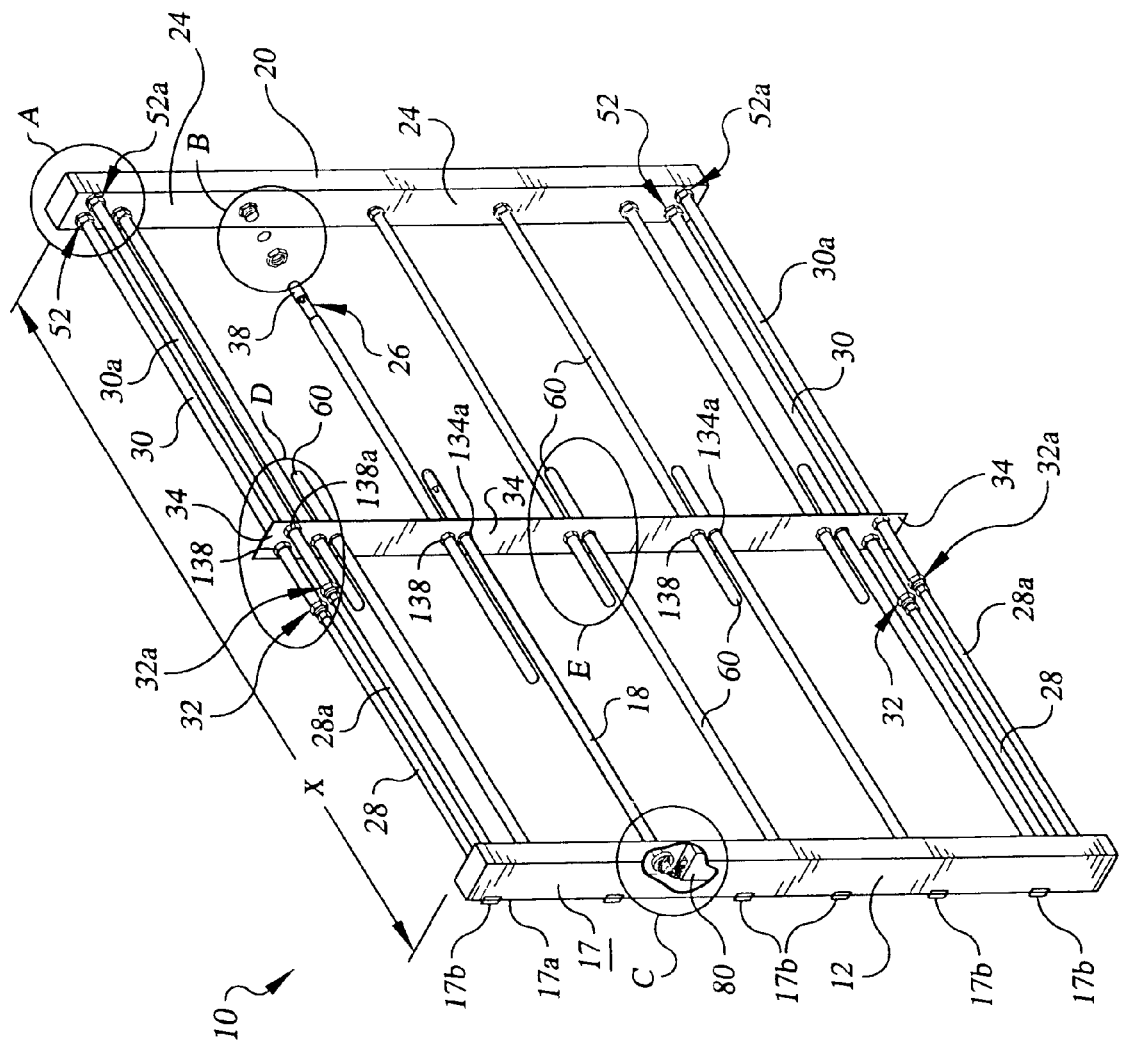
FIG. 1 is an isometric view of a fluid disinfection module in accordance with one embodiment of the invention.
Figure 2:
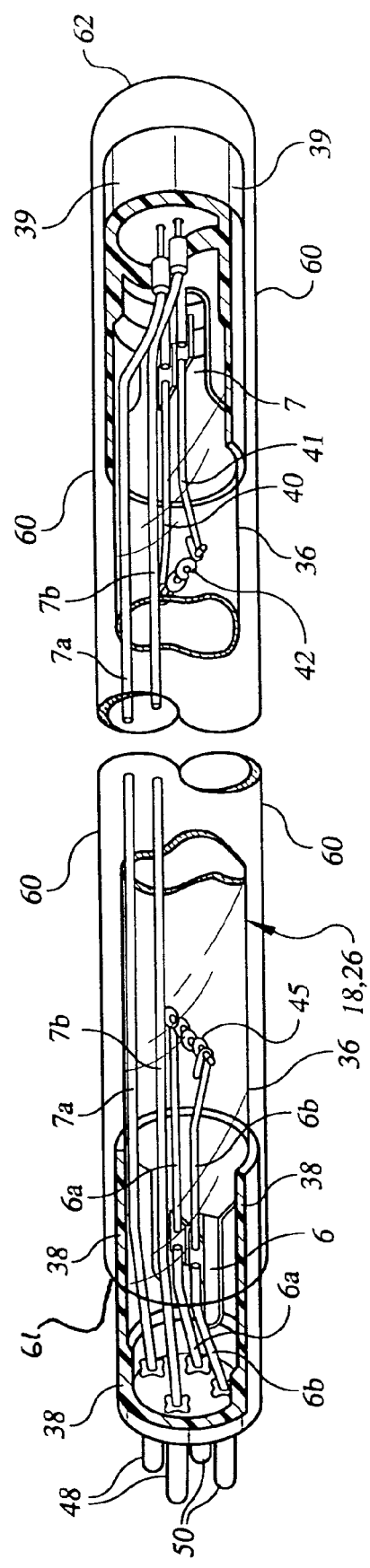
FIG. 2 is an elevated cross-sectional plan view of the quartz sleeve illustrated in FIG. 1 surrounding an ultraviolet lamp in accordance with an embodiment of the invention herein.

Referring to the drawings, specifically FIG. 1, there is shown for illustrative purposes only, a fluid disinfection module 10 constituting one embodiment of the invention herein. Module 10 is structured for adaptation to the confined spaces within a HVAC system of varying dimensions for the disinfection of air, and has a framework-type configuration comprising a first elongate housing 12 having a generally rectangular cross-section. As better shown in FIG. 3, housing 12 is provided with at least one opening 14 on one elongate side 16 thereof, preferably a plurality of such openings, for receiving therein for mounting with housing 12 a corresponding number of ultraviolet radiation sources in the form of elongate tubular ultraviolet ("UV") lamps 18, whose details are illustrated in FIG. 2. Referring to FIG. 4, module 10 also comprises a second elongate housing 20 similar to housing 12 in that it also has a generally rectangular cross-section provided with at least one opening 22 on one elongate side 24 thereof, preferably a plurality of openings. A corresponding number of ultraviolet radiation sources in the form of tubular UV lamps 26 are received in the respective openings 22 for mounting with housing 20. In forming the framework-like configuration of module 10 (see FIG. 1), housing 12 is provided with a pair of tubular support members 28,28a having a circular cross-section, one end of each member being secured to elongate side 16 by means of compression fittings 52,52a, respectively, the detail of which is partially illustrated in FIG. 5. Tubular support members 28,28a are arranged to laterally project from side 16 (shown in FIG. 3) in a substantially perpendicular direction towards housing 20.

Figure 1A:
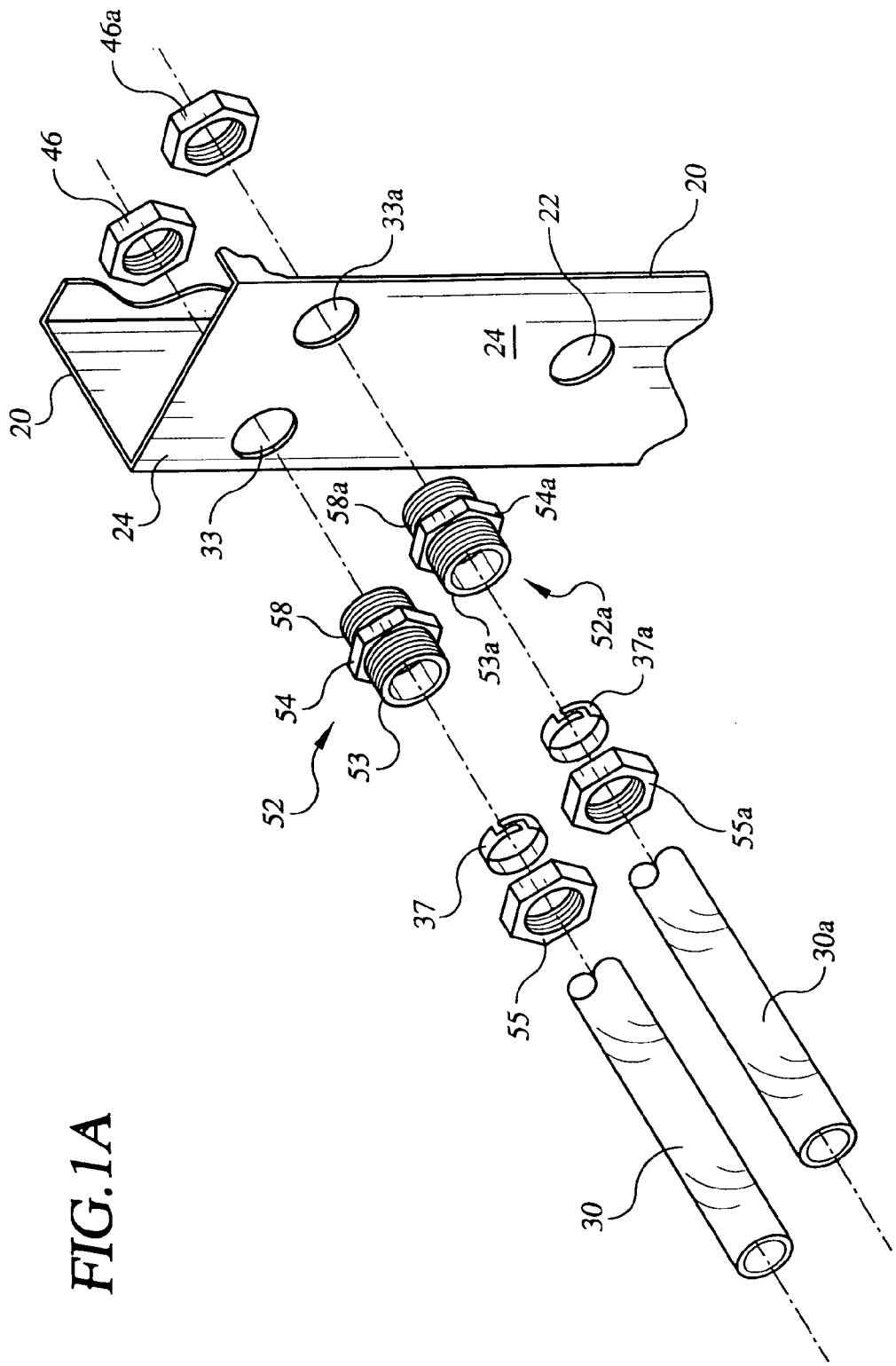
FIG. 1A is an exploded fragmentary isometric view of detail A illustrated in FIG. 1.
Figure 5A:
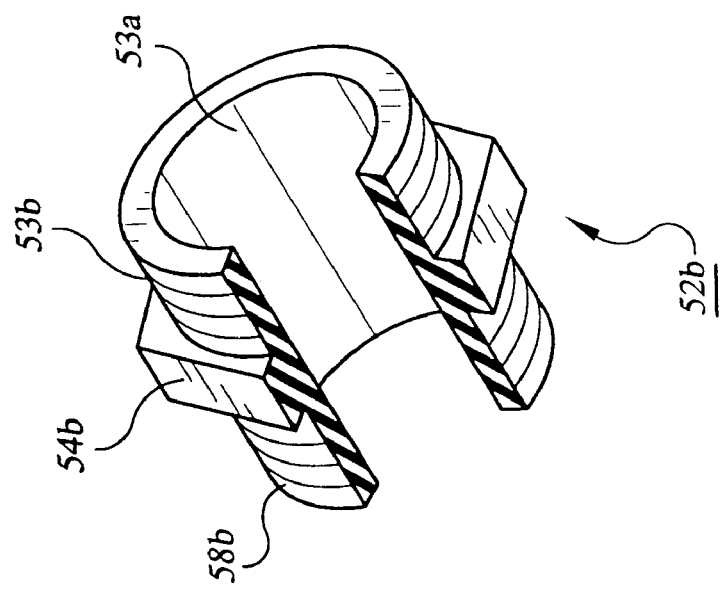
FIG. 5A is an enlarged segmented isometric view of compression fitting 52b illustrated in FIG. 3.
Figure 5:
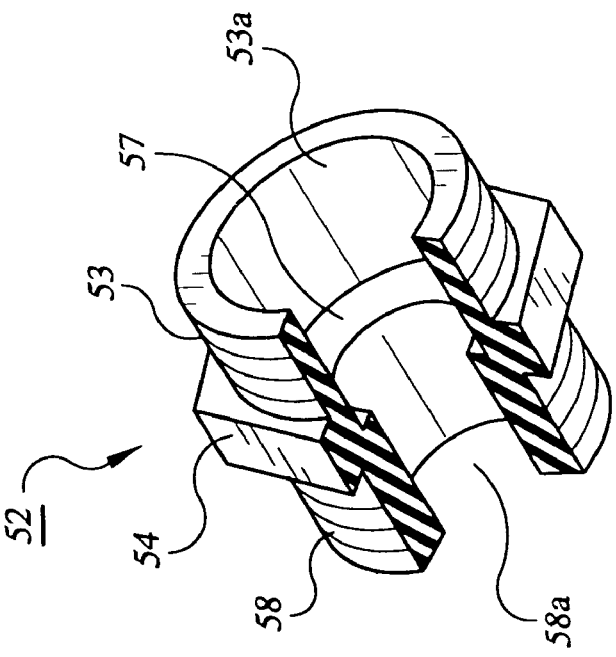
FIG. 5 is an enlarged segmented isometric view of compression fitting 52 illustrated in FIG. 4.

In similar fashion, a second elongate housing 20 is provided with a pair of tubular support members 30,30a, one end of each being secured to elongate side 24 of housing 20 in the manner illustrated in FIG. 1A. FIG. 1A enlarges on the area defined by Detail A shown in FIG. 1. While other configurations may be employed, the manner of the joinder of tubular support members 28,28a to housing 12 is identical to the joinder of tubular support members 30,30a to housing 20, i.e., by the use of compression fittings 52,52a. Referring to FIGS. 1A and 5, compression fittings 52,52a have exteriorly threaded annular extensions 53,53a and 58,58a projecting from either side of a hexagonal-shaped nut 54,54a, respectively. Annular extensions 58,58a are configured for slidable insertion through openings 33,33a provided in elongate side 24. Once hexagonal-shaped nuts 54,54a interface with the exterior surface of elongate side 24, locking nuts 46,46a positioned on the interior side of elongate side 24 are engaged with annular extensions 58,58a for the securement of compression fittings 52,52a to housing 20. Hexagonal-shaped nuts 54,54a and locking nuts 46,46a therefore function as flanges for the containment of elongate side 24 therebetween. As shown in greater detail in FIG. 5, annular extension 58 (as well as extension 58a) is sized to be smaller in diameter than annular extension 53 (and 53a), which results in the provision of an annular seat 57 located within the confines of compression fittings 52,52a. Therefore, when the ends of tubular support members 30,30a are inserted through compression nuts 55,55a and annular split rings 37,37a into compression fittings 52,52a, respectively, they will come to rest against annular seat(s) 57, the annular seat 57 being axially located in FIG. 5 within the confines of hexagonal-shaped nut 54. Annular split rings 37,37a, formed from a metal or plastic construction, are respectively sized to fit within compression nuts 55,55a which are configured for threaded engagement with annular extensions 53,53a. The engagement of compression nuts 55,55a with compression fittings 52,52a will cause split rings 37,37a to be compressed about the ends of tubular support members 30,30a, respectively, thereby securing the tubular support members to housing 20. In this manner, tubular support members 30,30a are enabled to laterally project from side 24 in a substantially perpendicular manner towards housing 12. The utilization of properly sized compression fittings 52,52a with tubular support members 28,28a also enables securement of those tubular support members to housing 12 in the same manner.

While other locations along the length of elongate sides 16 and 24 are possible, tubular support members 28,28a and 30,30a are positioned about and secured to the ends of their respective housings with compression fittings 52,52a such that they are in axial alignment with respect to each other. Each of the tubular support member pairs are sized in diameter for slidable insertion within the other. This arrangement allows the lateral distance x between housings 12 and 20 to be varied for enabling the placement and securement of module 10 within the receiving space of a HVAC system. Either pair of tubular support members 28,28a and 30,30a may have the smaller diameter and thereby serve as the male segment in their mateable relationship with each other. Alternatively, tubular support members 28 and 30a may have the smaller diameter and serve as the male components of the mateable relationship. Tubular support members 28,28a and 30,30a are maintained in fixed relationship with each other by the employment of a locking device 32 as identified by the circled Detail D in FIG. 1, and the details of which are described below and illustrated in FIGS. 7 and 8.

Equipped with the foregoing framework-like structure, the lateral distance x of module 10 can be varied to adapt to the corresponding dimension of the receiving space within a HVAC system. Accordingly, depending on the internal dimensions of the HVAC system for which the module is intended, UV lamps 18 and 26 can vary in length. For example, UV lamps 18 and 26, which include a lamp base 38 that supports electrical terminal pins 48,50 at one end of the lamp (see FIG. 2) for engagement with an appropriate socket retained by housings 12 and 20, are generally manufactured in variety of lengths by different manufacturers. Typical approximate lengths are 12 inches, 16 inches, 24 inches, 30 inches, 36 inches, 48 inches, and 61 inches, although any length can be ordered. For most industrial and commercial applications which employ large HVAC duct systems, the longer length UV lamps will be utilized, e.g., lengths of 33¼ (referred to as G-36 lamps) and 61³⁄₁₆ inches (referred to as G-64 lamps). When longer length UV lamps are utilized (such as the UV lamps 18 and 26 illustrated in FIG. 1.), it may become necessary to add structural support and rigidity to the framework-like module 10, and a cross support member may optionally be included with the module. As shown in FIG. 1, a cross support member 34 is included and configured to be mounted to tubular support members 30,30a and the quartz sleeves surrounding UV lamps 18 and 26. The implementation of cross support member 34 with tubular support members 30,30a is specifically identified by Detail D in FIG. 1, which is illustrated in greater detail in FIGS. 7-8. Detail E in FIG. 1 identifies the coupling of cross support member 34 with UV lamps 18 and 26 and is expanded upon in FIG. 11. And in Detail B in FIG. 1, which is expanded upon in FIGS. 2 and 4, UV lamps 18 and 26 may optionally be encased with quartz sleeves 60 to balance the operating temperature of the lamp and prevent it from being subjected to extreme temperatures that the air passing through a HVAC system may exhibit.

As illustrated in FIG. 1, each of UV lamps 18 and 26 projects from their respective housings 12 and 20 along a longitudinal axis that is substantially perpendicular to the opposing housing. The axes of UV lamps 18 are offset relative to the axes of UV lamps 26 in order to avoid contact of the lamps with each other when UV lamps 18 and 26 overlap. UV lamps 18 and 26 will always have a slight to moderate overlap in order to avoid the creation of a zone within which the air passing through the HVAC system will not be fully exposed to the effects of radiation emanating from the UV lamps. Detail B of FIG. 1 illustrates the manner of attachment of the UV lamps with their respective housings which is expanded upon in FIGS. 2-4.

FIG. 2 illustrates UV lamps 18 and 26 in greater detail. UV lamps 18 and 26 are conventional, low pressure, ultraviolet lamps whose multiple electrical terminal pins are contained at one end thereof for electrical connection with a power supply preferably contained within housings 12 and 20, respectively. In the embodiment illustrated in FIGS. 2-4, a two pairs of electrical terminal pins 48 and 50 are secured to and emanate from lamp base 38. The UV lamp of FIG. 2 comprises a vacuumed, quartz tubular portion 36, i.e., a "hard glass" lamp, that is sealed at the collapsed ends 6 and 7 thereof. It will be noted that in place of a "hard glass" lamp, a two- or four-pin "soft glass" UV lamp manufactured by the Phillips Corporation may be used which has a tubing that is permeable to ultraviolet light in the wavelength range that includes 254 nanometers. Each end of tubular portion 36 is respectively retained and supported by lamp bases 38 and 39 which may be formed from a suitable ceramic or plastic material, preferably molded plastic. Ends 6 and 7 contain respective electrode filaments 45 and 42. Lamp base 39 houses the ends of a pair of wires 40,41 emanating filament 42 through the sealed end 7 of tubular portion 36. A pair of lead wires 7a,7b connects respectively with wires 40,41 and extend along the outside of tubular portion 36 for connection with a pair of electrical pins 48 axially extending from lamp base 38. Filament 45 at the opposite end of tubular portion 36 is electrically coupled with conductor wires 6a,6b extending through collapsed end 6 which in turn are connected to the remaining pair of terminal pins 50 also axially extending from lamp base 38. When filaments 45,42 are supplied with electrical power, they serve to energize and vaporize mercury contained within vacuumed tubular portion 36. UV lamp 26 illustrated in FIGS. 1, 3-4, 10, and 15-16 have an identical construction for mounting with its respective housing 20, and like UV lamp 18, may be a "hard glass" or "soft glass" lamp. UV lamps 18 and 26 can optionally be provided with a protective quartz sleeve 60 whose purpose and function is described in greater detail below.

Figure 3:
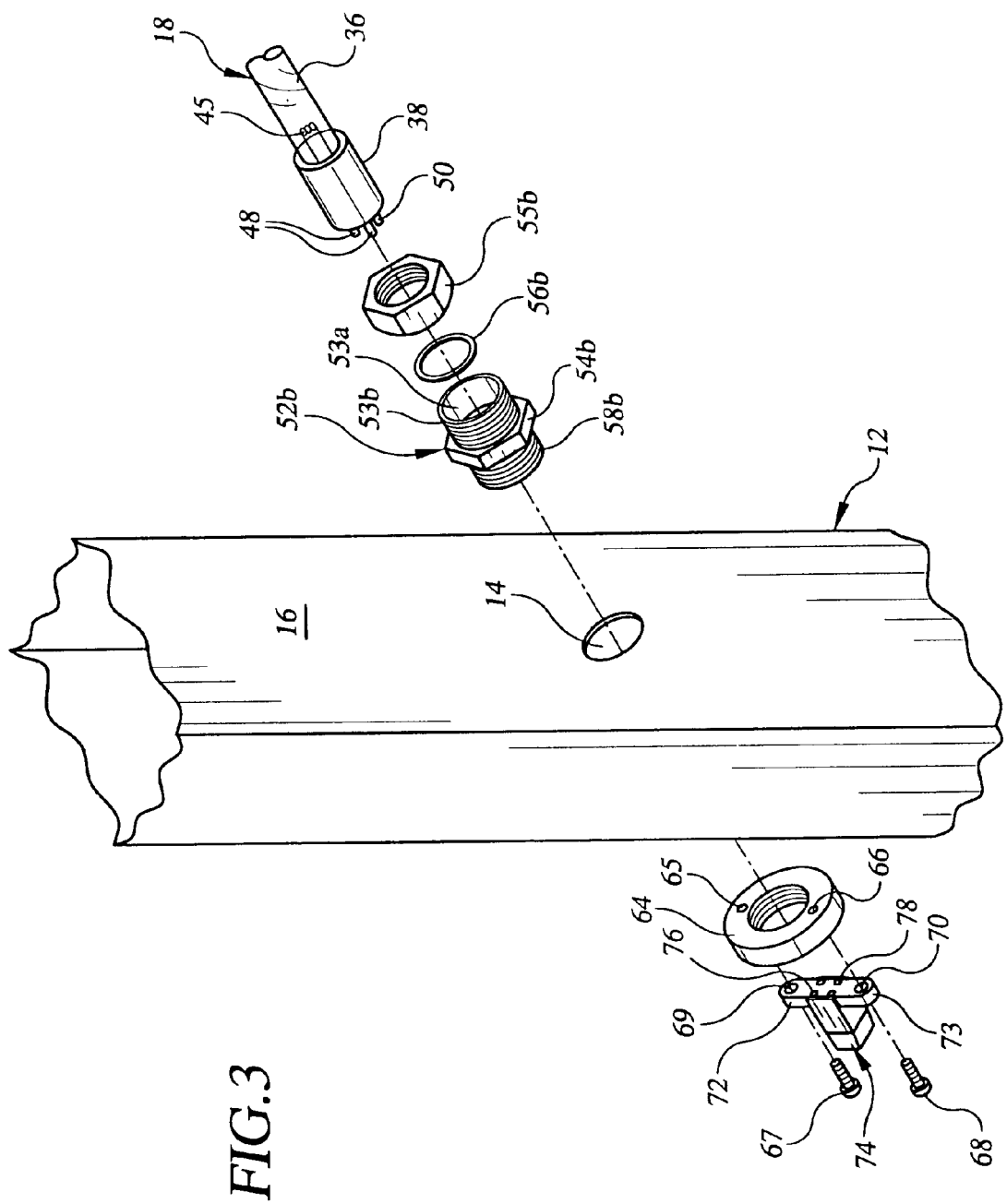
FIG. 3 is an exploded isometric view of detail B illustrated in FIG. 1.
Figure 4:
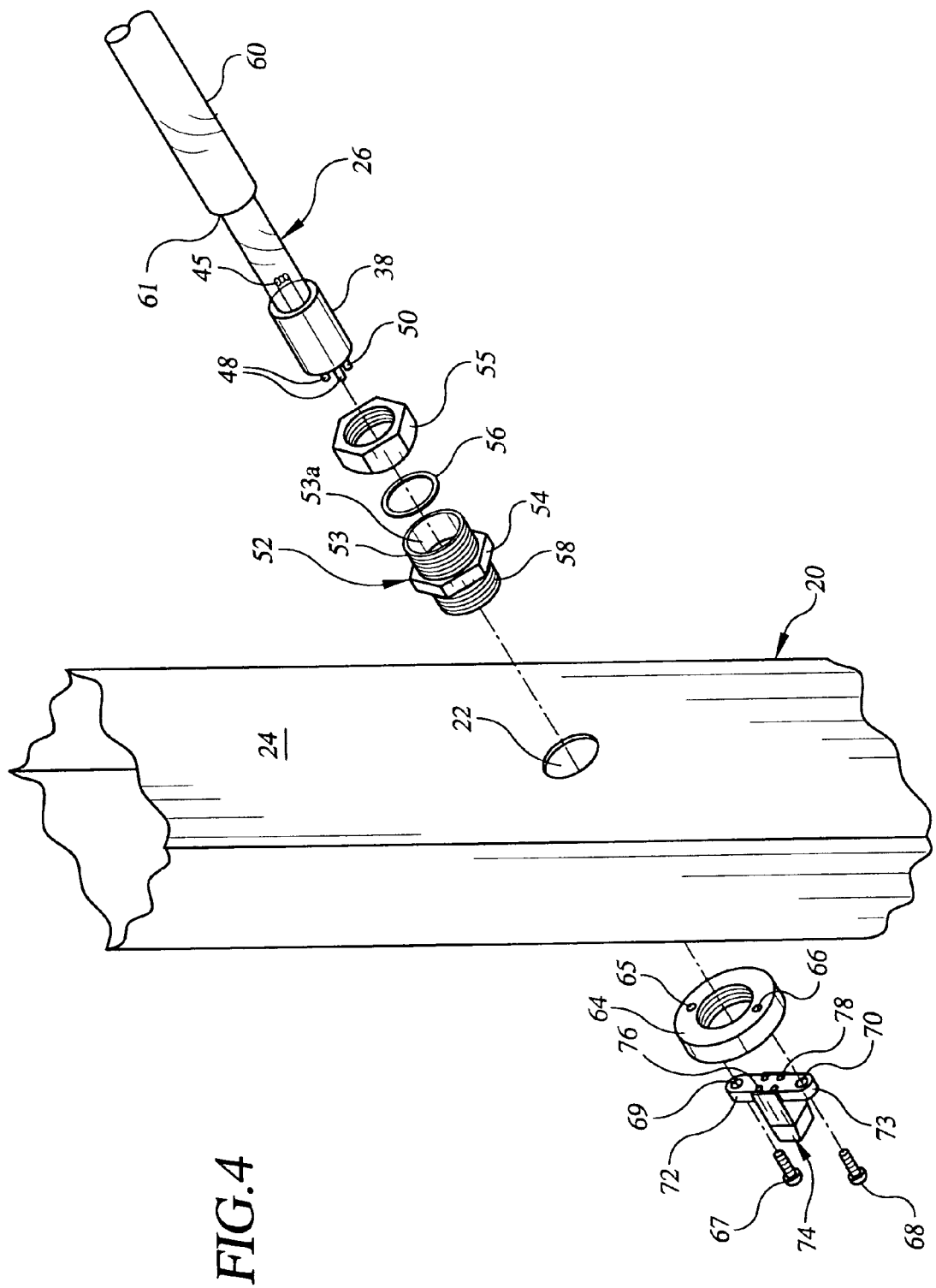
FIG. 4 is an exploded isometric view of another embodiment for detail B illustrated in FIG. 1.

UV lamps 18 and 26 may be secured to their respective housings 12 and 20 in any number of ways, an example of which is illustrated in FIG. 3. Referring to FIGS. 3 and 5A, a threaded compression fitting 52b has exteriorly threaded annular extensions 53b and 58b projecting from either side of and integral with a hexagonal-shaped nut 54b. As detailed in FIG. 5A, annular extension 58b is configured to be of the same diameter as extension 53b thereby providing a common annular opening 53a. Referring once again to FIG. 3, the diameter of annular extension 58b is sized to slidably extend through opening 14 of housing 12, and once inserted therein, the mounting of compression fitting 52b to elongate side 16 is undertaken by the threaded engagement of annular coupling member 64 with extension 58b. Annular coupling member 64 is configured in size to be greater than opening 14 and may take any shape or form to act as a flange for contact with the interior surface of elongate side 24. The coupling member may be manufactured from, for example, a hardened plastic material such as polyvinylchloride, although any metal construction of brass, steel, stainless steel, aluminum, cast zinc, etc. may be utilized. Hexagonal-shaped nut 54b and coupling member 64 therefore embrace elongate side 16 therebetween to fix compression fitting 52b to housing 12.

As shown in FIG. 3, annular coupling member 64 is provided with two threaded openings 65,66, for receiving a pair of fasteners, e.g., correspondingly threaded bolts 67,68, respectively, that are designed to pass through a pair of openings 69,70 contained within wing extensions 72,73 of electrical socket 74 (see FIG. 6) to secure the socket to coupling member 64. Electrical socket 74 connects with electrical terminal pins 48,50 by receiving them into electrical receptacles 76,78. As already noted above, annular coupling member 64 is configured in size to be substantially larger than opening 14 to act as a flange against the interior of elongate side 24, and in addition to provide a suitable support for wing extensions 72,73 of socket 74.

Once compression fitting 52b is secured to housing 12 along with the coupling of electrical socket 70 to coupling member 64, the mounting of UV lamp 18 follows. An annular O-ring 56b is provided and sized to fit within an internally threaded compression nut 55b. Compression nut 55b is configured for threaded engagement with annular extension 53b. The annular openings of the O-ring and compression nut are configured for slidably receiving lamp base 38 therethrough. Lamp base 38 of UV lamp 18 is then inserted through compression nut 55b, O-ring 56b, and into opening 53a of compression fitting 52b. Once inserted, the terminal pins 48,50 of lamp base 38 are engaged with their corresponding female electrical receptacles 76,78. The engagement of compression nut 55b with annular extension 53b will then cause O-ring 56b to be compressed about lamp base 38 for the securement of UV lamp 18 to compression fitting 52b and to housing 12. In this fashion, UV lamp 18 is enabled to laterally project from its respective housing 12 towards its opposite housing 20. UV lamp 26 may be secured to housing 20 in the same fashion.

As noted herein, and as best illustrated in FIGS. 2 and 4, each of UV lamps 18 and 26 may optionally be provided with a transparent protective sleeve, typically a quartz sleeve 60 that is pervious to the ultraviolet light emitted by UV lamps 18 and 26, or a sleeve constructed of ultraviolet light pervious materials such as KYNAR® or TEFLON®. Encasing the UV lamps with a transparent protective sleeve has several advantages. HVAC duct systems generally function by admitting air from an outside environment and then subjecting it to filtration, cooling and/or heating, and/or humidification, and finally transporting it through the HVAC duct system to a plurality of domestic rooms or commercial and industrial spaces, and even vehicles such as automobiles and public transport vehicles, e.g., airplanes, buses, trains, etc.

Temperature variations of the air passing through a HVAC system, depending on the air's treatment, are therefore inevitable and become one of the factors that determine the longevity and efficiency of a radiation lamp used for air disinfection. For example, as cooler air temperatures lower the skin temperature of the lamp's tubing, the operating temperature of the mercury vapor contained within the lamp's tubing will tend to drop. If the operating temperature is sufficiently lowered, the mercury vapor pressure will also be lowered and less ultraviolet radiation will be produced. Therefore, when heat is drawn away from the lamp by the cooler HVAC system air, the ultraviolet light output of the lamp will decrease. As shown in FIGS. 1 and 4, the utilization of UV lamps 18 and 26 that are encased with quartz sleeves 60 serves to balance the operating temperature of the UV lamps and prevent them from being subjected to extreme temperatures of the air passing through a HVAC system in which module 10 is disposed. Optimum performance of the lamps, accompanied by an increased longevity, is therefore provided.

As best shown in FIG. 2, quartz sleeve 60 has an open end 61 for receiving UV lamp 18 (as well as UV lamp 26) therein, and is closed at its opposite end with a dome-shaped end 62. The open end 61 is sized to slidably fit about the circumference of lamp bases 39 and 38. In addition, the length of quartz sleeve 60 is configured to allow the end of lamp base 39 to butt against the dome-shaped end 62 of quartz sleeve 60 with the open end 61 terminating at approximately the midpoint of lamp base 38. The foregoing will have the effect of concentrically centering the tubular portion 36 of UV lamp 18 within quartz sleeve 60 to avoid its contact with the sleeve's inside surface. UV lamps 18 and 26 may be fixed within their respective quartz sleeves 60 by the application of an appropriate fixative and sealant between the inside surface of the open end 61 of sleeve 60 and the outside surface of UV lamp base 38. An example of a fixative and sealant is an ultraviolet light curative epoxy cement available from Norland Products Inc. under the name of Norland Electronic Adhesive.

The mounting of the UV lamp and protective sleeve assemblies to their respective housings is accomplished in much the same way as the mounting of UV lamp 18 to housing 12 illustrated in FIG. 3. The exception is that a compression fitting of the type illustrated in FIG. 5 is used. Referring to FIG. 5, compression fitting 52, like compression fitting 52b, includes two annular extensions 53,58 axially extending from hexagonal-shaped nut 54. The annular opening 58a of extension 58 is smaller in diameter than the annular opening 53a of extension 53. Extension 58 terminates approximately internally of hexagonal nut 54 to provide an annular seat 57. Annular extensions 53,58 and hexagonal-shaped nut 54 combine to form an integrated compression fitting constructed of, for example, a metal material such as brass, steel, stainless steel, cast zinc, aluminum, etc. The annular opening 58a of extension 58 is sized to receive lamp base 38 therethrough, but not quartz sleeve 60. Only the opening 53a of annular extension 53, compression nut 55, and O-ring 54 is sized to receive the larger diameter quartz sleeve 60 therein. The annular seat 57 acts as a stop for the open end 61 of quartz sleeve 60 when the sleeve is mounted over UV lamp 26 and inserted into compression fitting 52.

FIG. 4 expands upon Detail B shown in FIG. 1 and illustrates the mounting of UV lamp 26 and its quartz sleeve 60 to housing 24. As with compression fitting 52b, the mounting of compression fitting 52 to housing 20 (see FIG. 4) is undertaken by inserting annular extension 58 through opening 22 of elongate side 24 and securing it to side 24 by the threaded engagement of interiorly threaded annular coupling member 64. The coupling of electrical socket 70 with coupling member 64 is the same as that described for the mounting of UV lamp 18 to housing 12 illustrated in FIG. 3. Once compression fitting 52 is secured to housing 20 along with the coupling of electrical socket 70 to coupling member 64, lamp base 38 containing quartz sleeve 60 mounted thereto (in the manner illustrated in FIG. 2) is inserted through compression nut 55, O-ring 56, and into the annular opening 53a of extension 53. The length of quartz sleeve 60 is such that lamp base 39 of UV lamp 26 (see FIG. 2) will interface against the dome-shaped end 62 of the sleeve. Once the lamp and its quartz sleeve are positioned in compression fitting 52, and its electrical terminal pins 48,50 subsequently connected to electrical socket 70, the engagement of compression nut 55 with annular extension 53 causes O-ring 56 to be compressed about quartz sleeve 60 for the securement of the lamp and sleeve to compression fitting 52 and to housing 20. As a result, UV lamp 26 and its protective quartz sleeve 60 are enabled to laterally project from their respective housing 20 towards its opposite housing 12. It will be understood that both UV lamps 18 and 26 may utilize protective sleeves as is illustrated in FIG. 1.

Figure 7:
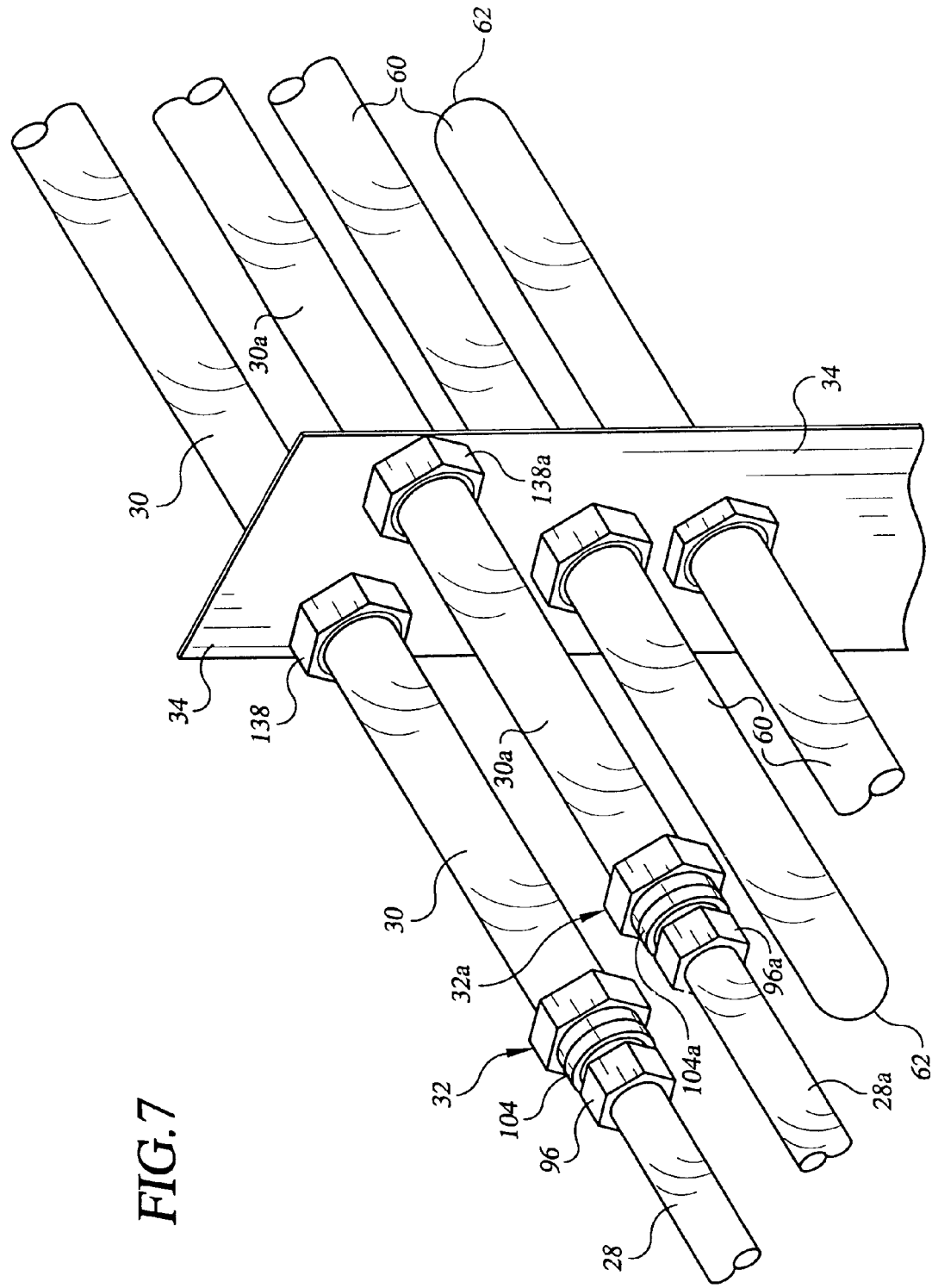
FIG. 7 is an enlarged isometric view of detail D illustrated in FIG. 1.
Figure 8:
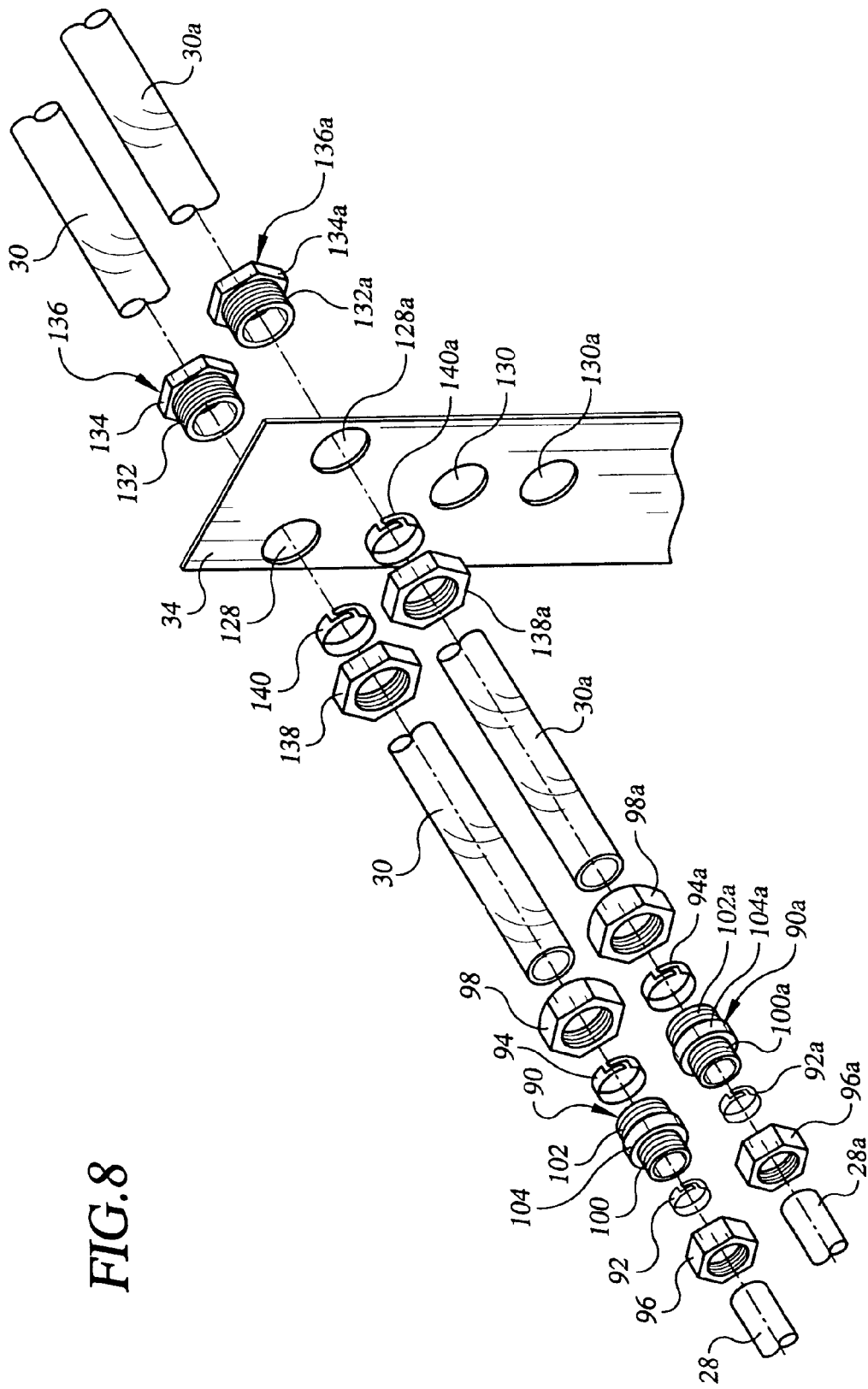
FIG. 8 is an exploded isometric view of detail D illustrated in FIG. 1.

As described hereinbefore and illustrated in FIGS. 1 and 7, housings 12 and 20 are formulated into a framework configuration by means of the slidable engagement of tubular support members 28,28a and 30,30a with each other which are held in place by locking devices 32,32a, respectively. Referring to FIGS. 7 and 8, locking devices 32,32a comprise compression fitting adaptors 90,90a, compression rings 92,92a and 94,94a, and compression nuts 96,96a and 98,98a, respectively. Each of compression fitting adaptors 90,90a, which is an integral fitting that can be formed from a plastic or metal material, e.g., polyvinylchloride, brass, galvanized steel, stainless steel, aluminum, etc., has exteriorly threaded annular extensions 100,100a and 102,102a extending in opposite directions from common members 104,104a, respectively. Annular extensions 100,100a necessarily have a smaller annular opening relative to annular extensions 102,102a for slidably receiving therethrough tubular support members 28,28a. Annular extensions 102,102a, on the other hand, have a larger opening for receiving tubular support members 30,30a therein the ends of which will come to rest against an annular stop (not shown, but similar to annular seat 57 of compression fitting 52 illustrated in FIG. 5) created by the respective termination of annular extensions 100,100a at or within the confines of common members 104,104a. Each of annular extensions 100,100a and 102,102a are respectively provided with correspondingly threaded compression nuts 96,96a and 98,98a which are respectively configured for slidable engagement with their corresponding tubular support members 28,28a and 30,30a. Together with concentric split rings 92,92a and 94,94a, corresponding compression nuts 96,96a and 98,98a will clamp the split rings about the exterior surface of their tubular support members 28,28a and 30,30a when the compression nuts are threaded onto their respective annular extensions for locking the tubular support members in place. With this arrangement, the lateral distance x between housings 12 and 20 (see FIG. 1) can be adjusted to the corresponding inner lateral dimensions of the receiving space within the HVAC system by sliding tubular support members 28,28a within tubular support members 30,30a and locking them in place with locking devices 32,32a.

Figure 9:
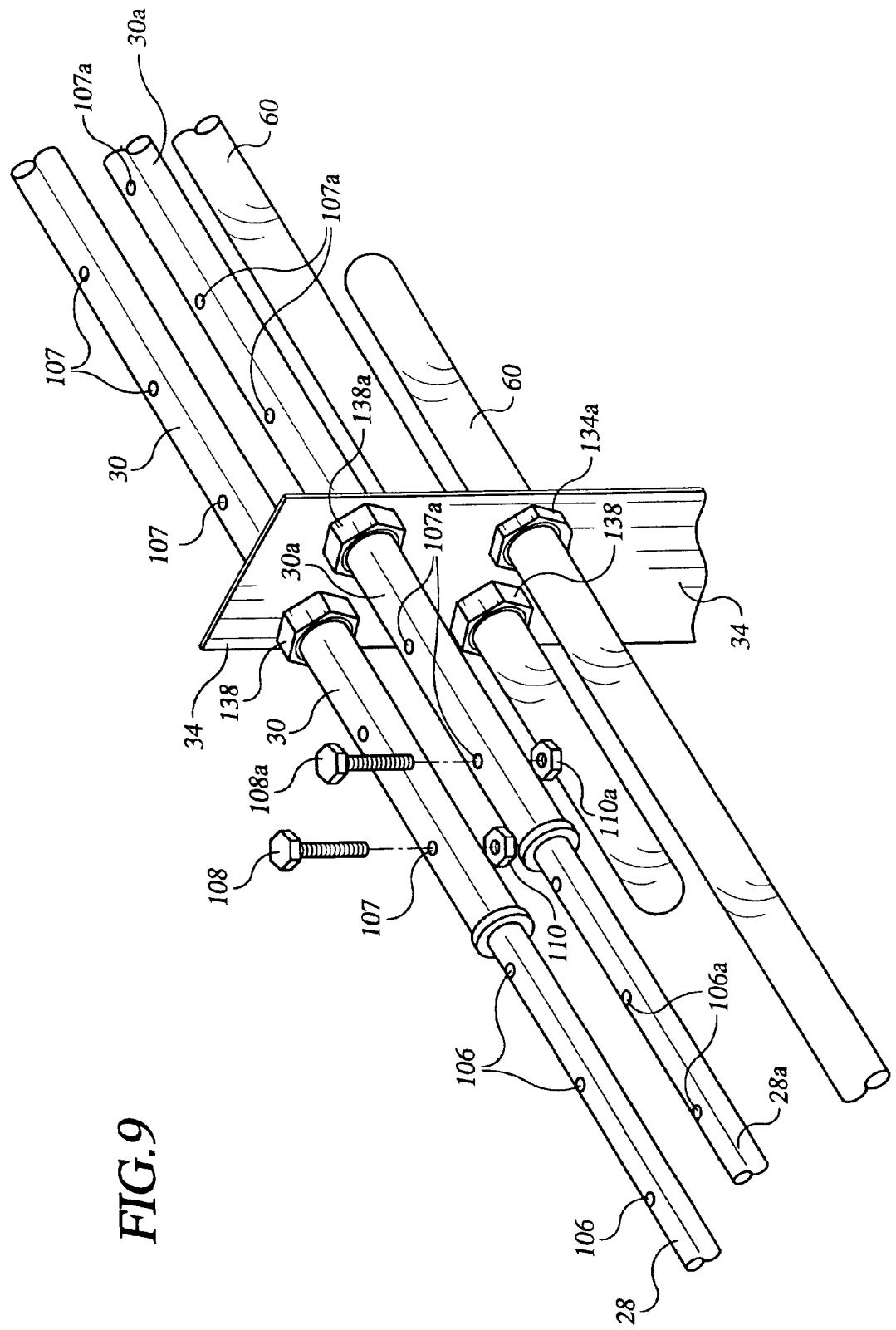
FIG. 9 is an isometric view of another embodiment of the invention illustrated in FIG. 7.

An alternative locking device for maintaining tubular support members 28,28a and 30,30a in place is illustrated in FIG. 9. In this embodiment, each of tubular support members 28,28a and 30,30a is provided with a series of openings 106,106a and 107,107a, respectively, on opposite sides of and along the length thereof for receiving therethrough threaded bolts 108,108a for engagement with correspondingly threaded nuts 110,110a. This has the effect of securing the respective tubular support members 28,28a and 30,30a to each other. Openings 106,106a and 107,107a are incrementally spaced apart along each of their respective tubular support members 28,28a and 30,30a such that openings 106, 106a will be in alignment with openings 107,107a when the insertion of tubular support members 28,28a into tubular support members 30,30a is varied by a predetermined distance. The predetermined distance is established by the spacing of openings 107,107a along the length of tubular support members 30,30a identically with the spacing of openings 106,106a along tubular support members 28,28a. This facilitates the insertion of threaded bolts 108,108a into openings 106,106a and 107,107a.

Figure 10:
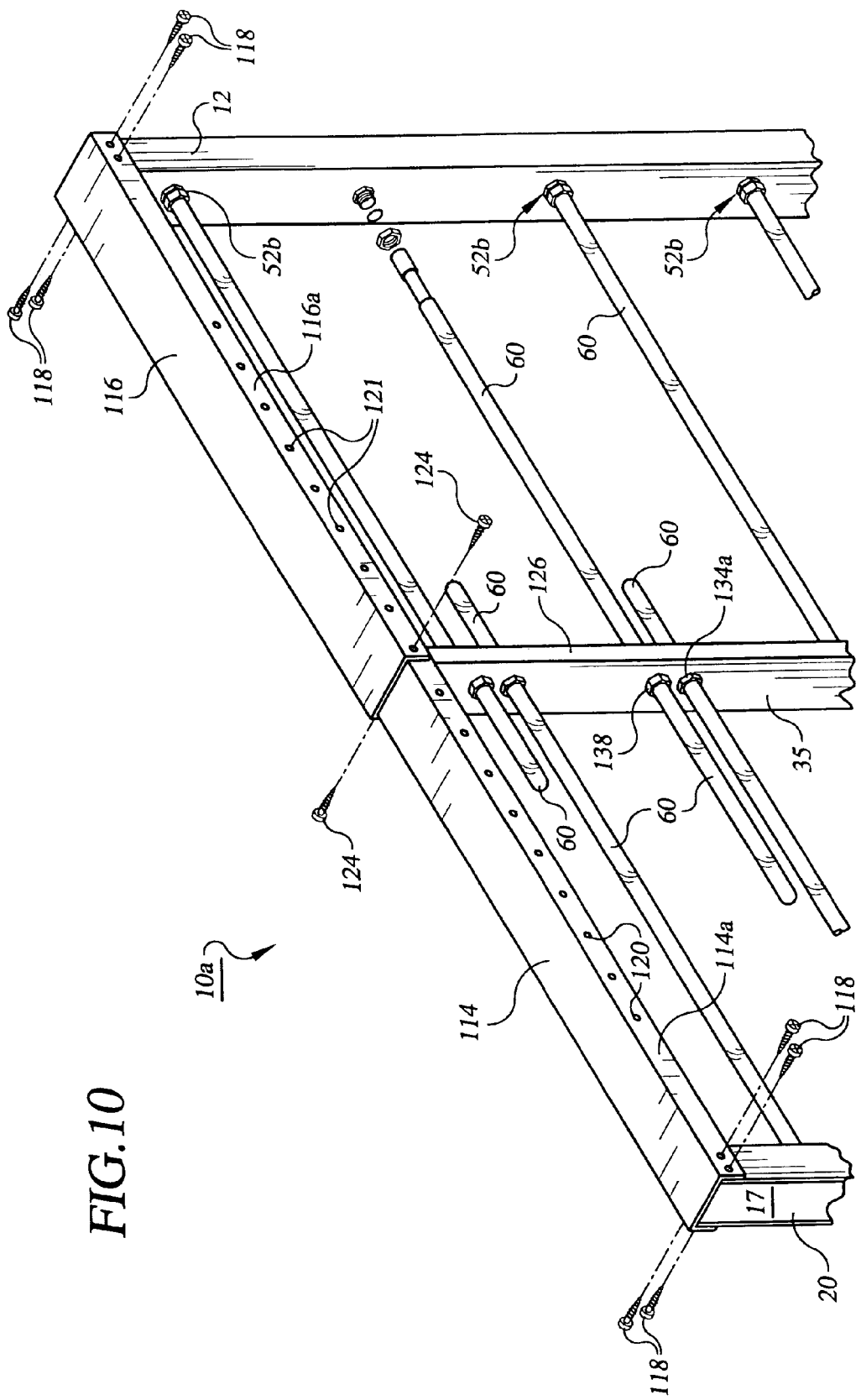
FIG. 10 is a partial isometric view of yet another embodiment of the invention illustrated in FIG. 1.

Another embodiment for varying the lateral distance x between housings 12 and 20 is illustrated in FIG. 10 wherein in place of tubular support members 28,28a and 30,30a, or in conjunction therewith, channel support members 114 and 116, disposed at both ends of housings 12 and 20, are used as the first and second housing support structures, respectviely, for establishing a framework-like module 10a. Accordingly, the width of the channel of channel support member 114 is configured in size for placement over and for encompassing the end of housing 12 as shown in FIG. 10. In like manner, one end of channel support member 116 is placed over and encompasses the end of housing 12. The respective ends of channel support members 114 and 116 may be fastened to their housing ends by any conventional means, for example, by the use of threaded sheet metal screws, bolts, or the like, inserted through the sides of the channel members into elongate sides 14 and 24 of housings 12 and 20, respectively. Sheet metal screws 118 are illustrated in FIG. 10.

Channel support members 114 and 116 are configured in size such that one will be slidably received within the channel of the other. As shown in FIG. 10, channel support member 114 is slidably disposed within channel support member 116. As with tubular support members 28,28a and 30,30a, the respective side walls 114a and 116a of channel support members 114 and 116 are provided with a plurality of spaced-apart openings 120,121, respectively, along the length thereof for receiving threaded bolts 124 when the openings 120,121 are in alignment with each other. In order to adjust the lateral distance between housings 12 and 20, channel support members 114 on both ends of housing 20 are slid into the corresponding channel support members 116 of housing 12 to a desired depth. Once openings 120,121 are aligned, channel support members 114 and 116 are fastened to each other by the insertion of threaded bolts 124, preferably in more than one openings 120,121 along the length of channel support member 116 to add rigidity to the combined channel support members 114,116.

It will be understood that any number and variety of mechanisms may be used to detachably secure the first and second housing support structures to each other, including, for example, a locking device that utilizes an annular compression fitting such as that identified by reference numerals 32 or 32*a* illustrated in FIG. 7 when the support structures are of a tubular construction, or a threaded screw or nut-and-bolt assembly when slidably engaged channels are used as illustrated in FIG. 9. It will also be appreciated that tubular support members 28,28*a* and 30,30*a*, as well as channel support members 114 and 116, may be secured to each other in other ways. For example, once the mating of the respective support members is undertaken and the lateral distance x between housings 12 and 20 is fixed, they can be fixed to each other by simply drilling one or more holes through the members, and inserting through the hole(s) an appropriate locking device, such as a nut and bolt combination, locking pin, etc.

Figure 11:
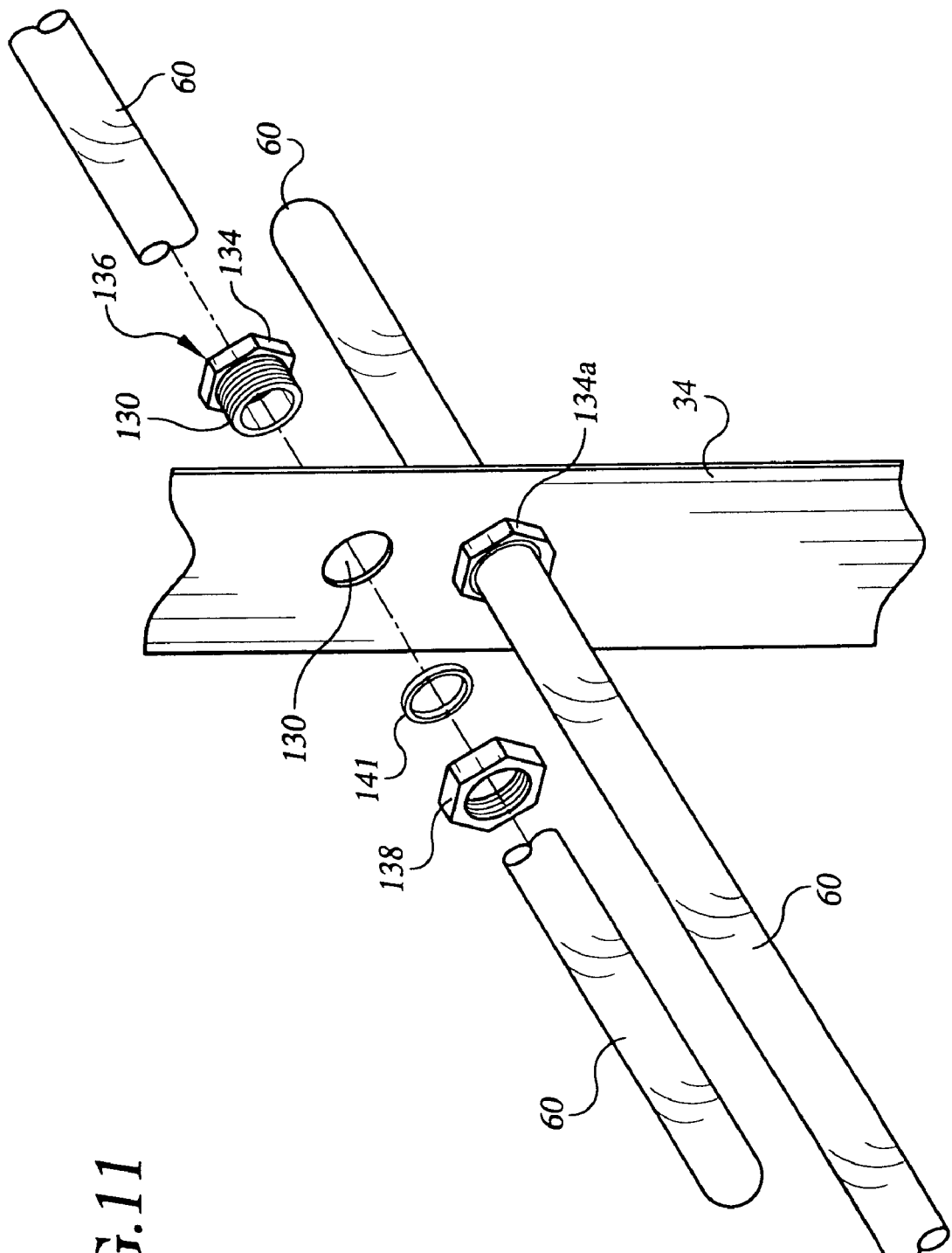
FIG. 11 is a partially exploded isometric view of detail E illustrated in FIG. 1.

As indicated hereinbefore, when it is desired to utilize longer length UV lamps within module 10, a cross support member may optionally be incorporated for adding rigidity and structural support to the framework-like configured module 10. The cross support member 34 illustrated in FIGS. 1, 8 and 11 is of an elongate rigid construction formed from metal or plastic and provided with a plurality of openings 128,128*a* to accommodate the slidable receipt therethrough of tubular support members 30,30*a*. Openings 130,130*a* are also provided for slidably receiving therethrough the corresponding quartz sleeves 60 of UV lamps 18 and 26, respectively, or simply the lamps themselves. As shown in greater detail in FIG. 8, openings 128,128*a* are sized to slidably receive therethrough exteriorly threaded annular extensions 132,132*a* emanating from a hexagonal-shaped nut 134,134*a* of compression fittings 136,136*a*, respectively. The annular compression fittings 136,136*a*, along with correspondingly threaded compression nuts 138,138*a* and compression rings 140,140*a*, are sized to be slidably mounted onto tubular support members 30,30*a* on either side of cross support member 34, and when it is desired to secure the cross support member in place to tubular support members 30,30*a*, compression rings 140,140*a* are placed over annular extensions 132,132*a*, respectively, followed by the mounting of compression nuts 138,138*a* thereto. The completed assembly is illustrated in FIG. 7.

As shown in FIGS. 9 and 11, cross support member 34 may also be secured to quartz sleeves 60 of UV lamps 18 and 26 in a similar fashion by securing compression nuts 138,138*a* to compression fittings 136,136*a* mounted about the quartz sleeves 60 on either side of cross support member 34. Instead of using compression rings 140,140*a*, which are usually made of metal for compression about tubular support members 30,30*a*, resilient O-rings 141 may be used for interfacing between the surface of quartz sleeve 60 and compression fittings 136,136*a* in the same as manner described for O-ring 56 used for securing the quartz sleeve/UV lamp assembly to housing 12 illustrated in FIG. 3. It is preferable that the resilient O-rings described herein be impervious to the deleterious effects of ultraviolet light, and as such can be of a TEFLON® construction.

In the embodiment illustrated in FIG. 10, cross support member 35 may take the form of a channel when it is desired to utilize longer length UV lamps within module 10*a*. The ends of side walls 126 of cross member 35 are provided with an opening (not shown) that is in alignment with openings 120,121 of channel support members 114 and 116, respectively, so that the same threaded bolts 124 can be used to secure cross member 35 and channel support members 114 and 116 to each other. Openings identical to openings 130, 130*a* for cross support member 34 illustrated in FIGS. 8 and 11, along with locking devices in the form of compression fittings 136,136*a* and compression nuts 138,138*a*, are also provided in cross member 35 for the receipt therethrough and support of the quartz sleeve/UV lamp assemblies projecting from housings 12 and 20.

It will be understood that if quartz sleeves 60 are omitted from the air disinfection module, along with compression fittings 136,136*a* used to secure the quartz sleeves to cross support members 34 and 35 (see FIG. 11), the openings 130 in cross support members 34 and 35 will be in direct contact with the tubular portion 36 of UV lamps 18 and 26. Moreover, if cross support members 34 and 35 are of a metallic construction, such as aluminum or stainless steel, the contact of the lamp tubing with the metal cross support member may contribute to "cold spots" on the surface of the lamp's tubing which may lead to a condensation of mercury vapor in that area of contact with the lamp. Since ultraviolet light is created by the vaporization of the lamp's mercury, any compromise in vaporization will lead to an inefficient operation of the lamp and contribute to its shortened operating life.

As a result, and in place of compression fittings 136,136*a*, openings 130 in support members 34 and 35 may be provided with a resilient grommet whose construction is preferably impervious to the deleterious effects of ultraviolet light, e.g., EPDN (VITON®). The resilient grommet is configured for slidably receiving and maintaining in place UV lamps 18 and 26, and will typically have a slight resistance fit with the tubular portion 36 of the UV lamps for their stationary positioning relative to cross support members 34 or 35 as the case may be.

Figure 6:
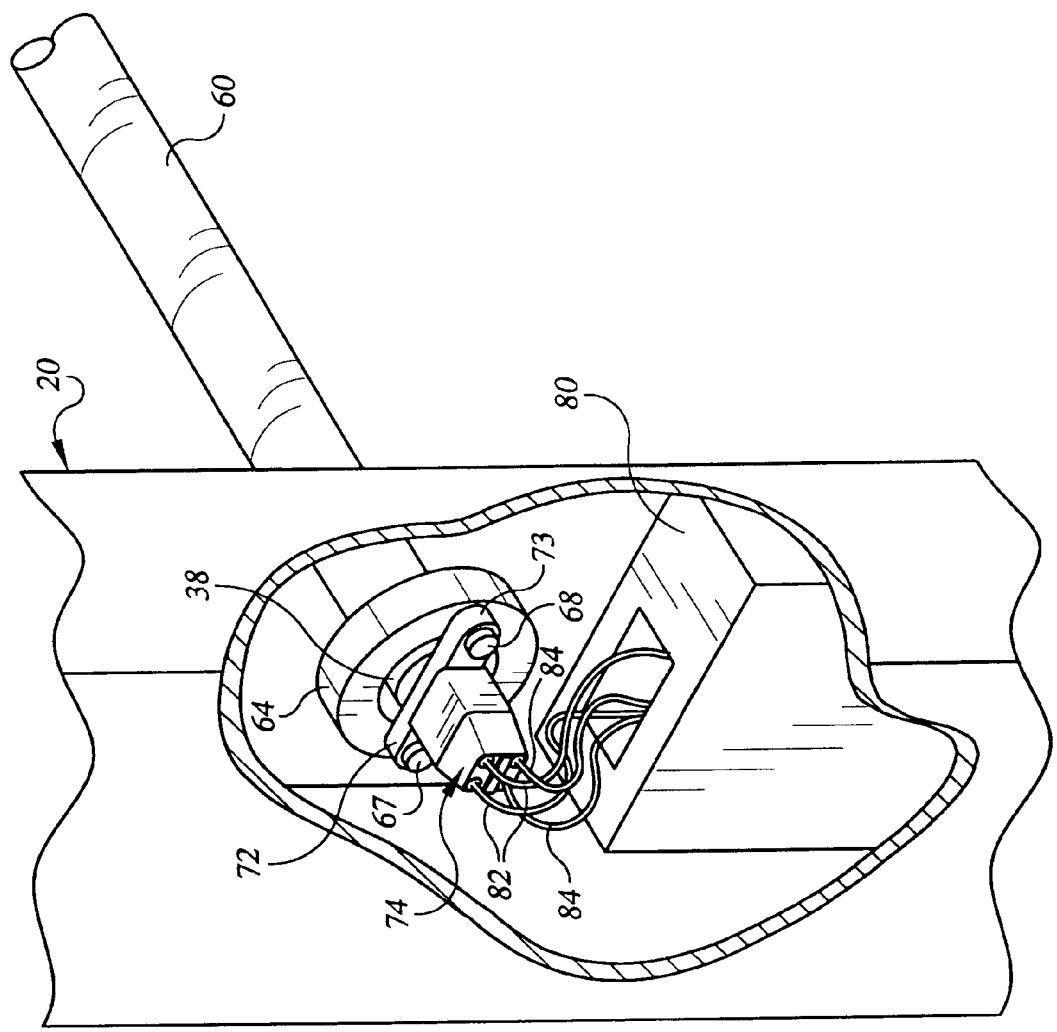
FIG. 6 is an enlarged isometric view of detail C illustrated in FIG. 1.

As illustrated in FIGS. 2, 4 and 6, the electrical terminal pins 48,50 of UV lamps 18 and 26 are electrically connected to one or more sources of electrical power, such as ballast 80, via electrical socket 74 provided with electrical wires 82 and 84. It will be appreciated that the longer length UV lamps can accommodate commercial duct sizes that are relatively large, usually encountered in large office buildings. Generally, for lamps greater than about 33 inches in length, one ballast will be required to power one lamp, but for UV lamps that are less than about 33 inches in length or much less, one ballast can supply power to two or more UV lamps depending on the size of the lamp. The electrical characteristics of the ultraviolet lamp and ballast should complement each other in order to contribute to the lamp's operational efficiency and longevity. In one embodiment, and for economy of space within a HVAC system, it is desirable to position and fix the ballasts on or within the respective housings 12 and 20, preferably therein utilizing appropriate wiring or cables to connect the ballasts 80 to a power source exterior of modules 10 or 10*a*. The power source for connecting the wiring and cables is typically located exterior of the HVAC system within which the fluid disinfection module is disposed.

Referring to FIG. 1, access to the interior of housings 12 and 20 may be gained by providing appropriate openings and/or removable covers therefor in the elongate side 17 opposite to side 16 of housing 12. A similar arrangement can be provided for housing 20. Alternatively, as shown in FIG. 1, the entire or partial length of elongate side 17 can be arranged in a "hinge" configuration with housing 12 whereby the respective entire or partial length of elongate edge 17*a* of elongate side 17 is hinged to the housing with hinges 17*b* to provide an access panel to the interior thereof.

Figure 12:
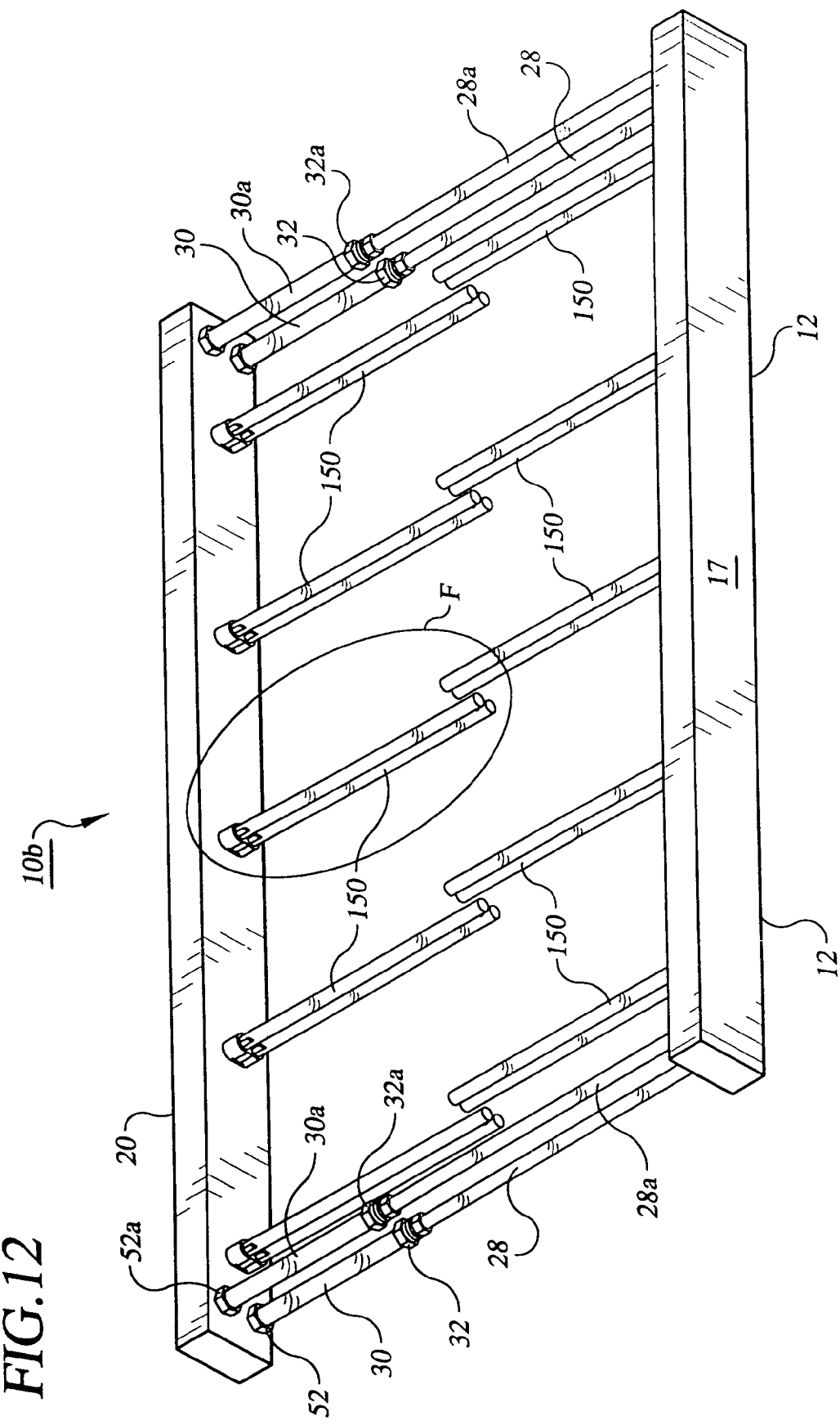
FIG. 12 is an isometric view of a fluid disinfection module according to another embodiment of the invention.

In place of the straight length UV lamps illustrated in FIGS. 1 and 2, or in combination therewith, "twin-tube" radiation sources can be utilized for formulating an fluid disinfection module 10b as illustrated in FIG. 12. Module 10b is essentially the same as module 10 with the exception that twin tube UV lamps 150 are utilized in place of the UV lamps 18 and 26 illustrated in FIG. 1. Moreover, because of the rigidity of twin tube UV lamps 150 and their manner of attachment to housings 12 and 20, no cross support member 34 is usually required for support these types of lamps. As shown in greater detail in FIG. 13, twin tube UV lamp 150, which may have a "hard glass" or "soft glass construction, comprises two hollow elongate tubes 152,153 that are parallel to each other along their longitudinal lengths, and joined together about end portion 154 of lamp 150 by a short hollow connecting tube 155. The electrodes 157,158 of respective tubes 152,153 are disposed about end 156 opposite to end 154 of the lamp tubes, and are connected respectively, via lead wires (not shown), with terminal pins 159,160 disposed in and extending from a common lamp base 162. Lamp base 162 contains a slight indentation 163 in the top-middle and bottom-middle portions thereof to form respective lips 164 at the end of the lamp base 162. The lips 164 and terminal pins 159,160 are configured for engagement with corresponding catches 165 and terminal pin receptacles 167,168 of socket 170 which is mounted to elongate side 16 of housing 12 by the threaded engagement of threaded bolts 172, inserted through flanges 173 disposed on either side of socket 170, with openings 174 provided in elongate side 16 for that purpose. Elongate side 16 is provided with a rectangular opening 176 to accommodate the receipt therethrough of electrical transmission means in the form of connecting wires 178,179 leading from terminal pin receptacles 167,168, respectively, to a ballast (not shown) that may be located within or without housing 12 or disposed about another part of module 10b.

FIG. 14 illustrates another embodiment of a twin tube ultraviolet lamp in the form of U-shaped UV lamp 182 which closely resembles twin tube UV lamp 150. As the name implies, U-shaped UV lamp 182 has a U-shaped tubing portion 184 at the end of the lamp opposite to lamp base 170 that connects elongate tubes 152,153, and in all other respects is identical to twin tube UV lamp 150. As shown in FIG. 14, socket 170 has been mounted and secured to elongate side 16, and the terminal pins 159,160 projecting from lamp base 170 of U-shaped UV lamp 182 has been inserted into socket 170 for secure mounting of the lamp to housing 12. It will be appreciated that socket 170 can be mounted interiorly of housing 12 to the opposite side of elongate side 16 provided that an appropriate opening is provided in elongate side 16 for mounting the lamp to socket 170.

Figure 15:
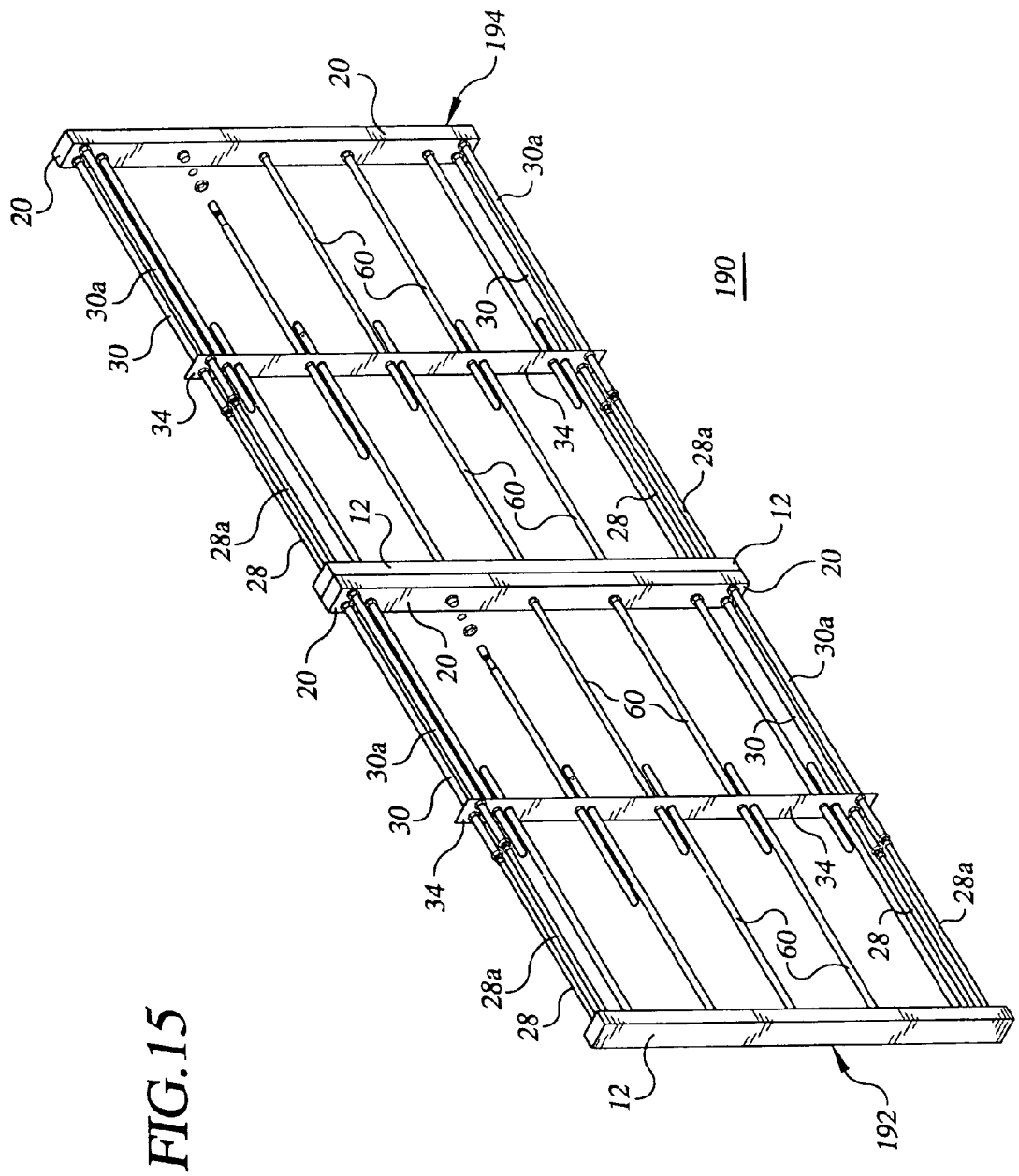
FIG. 15 is an isometric view of a pair of the fluid disinfection modules illustrated in FIG. 1, each module being assembled to each other to form an array in accordance with another embodiment of the invention.

In accordance with another embodiment of the invention, a multiplicity of modules 10, 10a and/or 10b can be used to form an array in which the modules are disposed and assembled laterally of each other. An array of modules, i.e., two or more, is generally used in the circumstance when the lengths of the UV lamps contained in a single module, e.g., module 10 illustrated in FIG. 1, and the resulting lateral distance x will not be sufficient for extending across the entire cross section of a given HVAC system or a particular air duct. Accordingly, in another aspect of the invention, and as shown in FIG. 15, an array 190 of two fluid disinfection modules 192 and 194 is formed by securing the adjacent housings of each module to each other, in this case, second housing 20 of module 192 and first housing 12 of module 194. These housings may be secured to each by any conventional means (not shown), for example, by using brackets or clamps, by securement to a common brace, rail or support, or by simply fastening the housings to each other using a nut/bolt arrangement or screws.

The array of modules may also include an arrangement whereby the individual modules are stacked, one over the other. In one embodiment, module 192 as shown in FIG. 15 will overlie the module 194, in which case, housing 12 of module 192 will overlie housing 12 of module 194. Another arrangement is to have housing 12 of module 192 overlie housing 20 of module 194, which in effect provides a lateral arrangement of the modules in which they are "staggered". In the latter arrangement, the overlapping of the housings 12 and 20 reduces the creation of any "blind" spaces within the HVAC system to which the ultraviolet light emanating from UV lamps 18 and 26 would not be exposed to.

Figure 16:
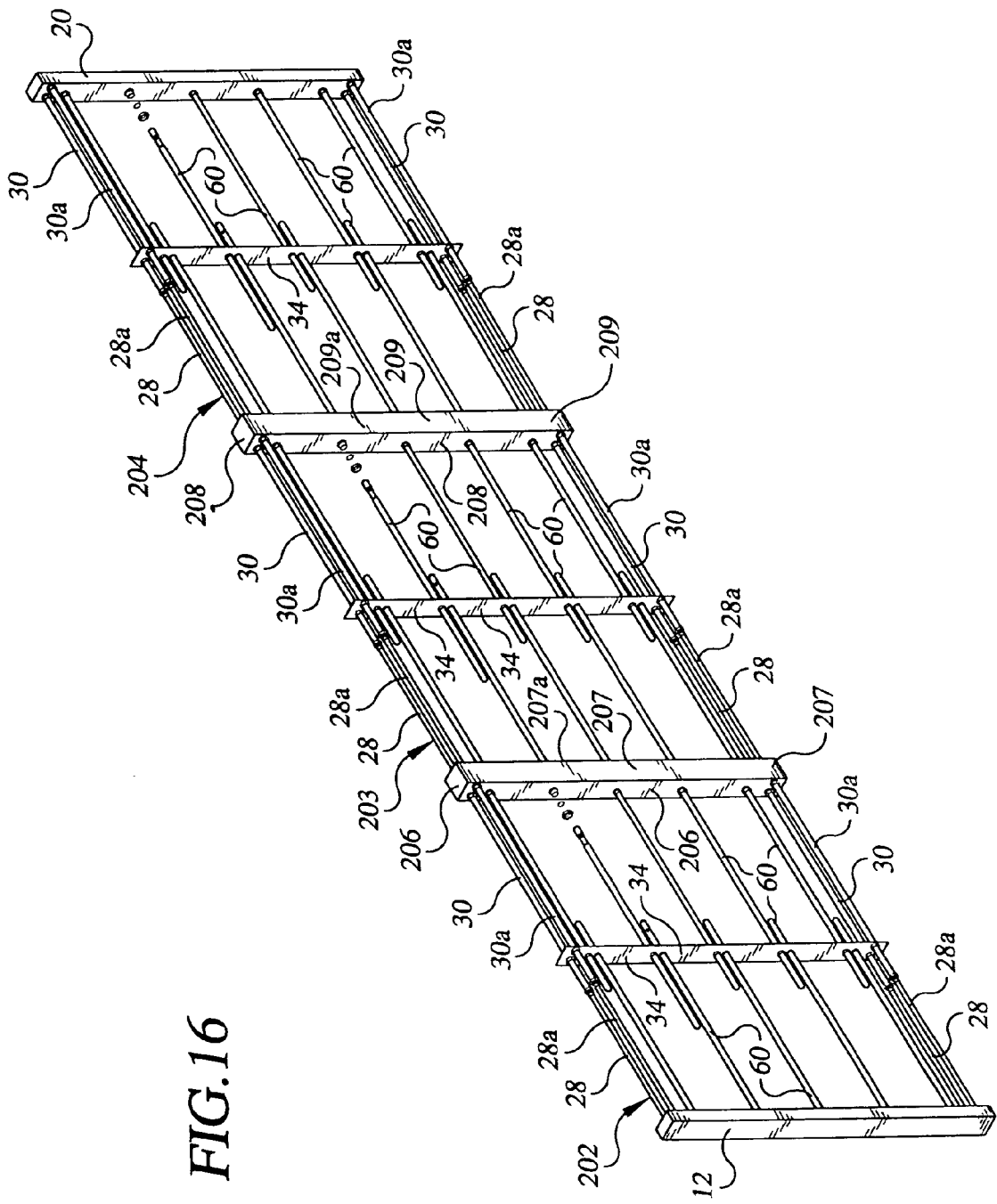
FIG. 16 is an isometric view of a plurality of the modules illustrated in FIG. 1, each module being assembled to each other with a common housing to form an array in accordance with yet another embodiment of the invention.

FIG. 16 illustrates another array 200 in which a greater number of fluid disinfection modules may be used to extend across exceptionally large ducts generally found in industrial plants and complexes. In the illustration shown, array 200 comprises three fluid disinfection modules 202, 203,204, although it will be understood that a greater number of modules may be utilized to formulate array 200 if circumstances warrant. Array 190 differs from array 200 in that air disinfection modules 202, 203 and 203, 204 share the same housings 206,208, respectively. In all other respects, modules 202,203, 204 are the same as module 10 illustrated in FIG. 1. Housing 206 has one end of tubular members 28,28a of module 203 secured to one side thereof with the opposite ends being slidably engaged and secured with tubular members 30,30a projecting from housing 208. In like manner, one end of tubular members 30,30a are secured to the opposite side of housing 206 while the opposite ends of tubular members 30,30a are slidably engaged and secured with tubular members 28,28a projecting from housing 12. Housing 208 has the same kind of arrangement. One end of tubular members 28,28a of module 204 are secured to and project from one side of housing 208 with the opposite ends of tubular members 28,28a being slidably engaged and secured with tubular members 30,30a projecting from housing 20. Cross support members 34 of modules 202,203,204 are engaged with and secured to tubular members 30,30a and quartz sleeves 60 in the same manner illustrated for module 10 in FIGS. 7, 8 and 11. Also, each of housings 206 and 208 receive and support either the UV lamp by itself or the UV lamp and protective sleeve assemblies on either sides thereof in the same manner illustrated for housings 12 and 20 in FIGS. 3, 4 and 5.

Inasmuch as housings 206,208 will contain an increased number of ballasts, electronics and wiring for powering both UV lamps 18 and 26, the physical capacity of these housings will be increased, either in the direction of the lateral plane of array 200 or in a direction perpendicular to the lateral plane. It is preferable to have the lateral width of housings 206 and 208 the same as housings 12 and 20 in order to avoid the creation of a space within the HVAC system to which the ultraviolet light emanating from UV lamps 18 and 26 would not penetrate. Access to the increased size of housings 206, 208 may be gained by arranging the entire or partial length of their respective elongate sides 207,209 in a "hinge" configuration whereby the respective entire or partial length of elongate edges 207a,209a of respective elongate sides 207,209 are hinged to housings 206,208 to provide an access panel to the interiors thereof.

Figure 17:
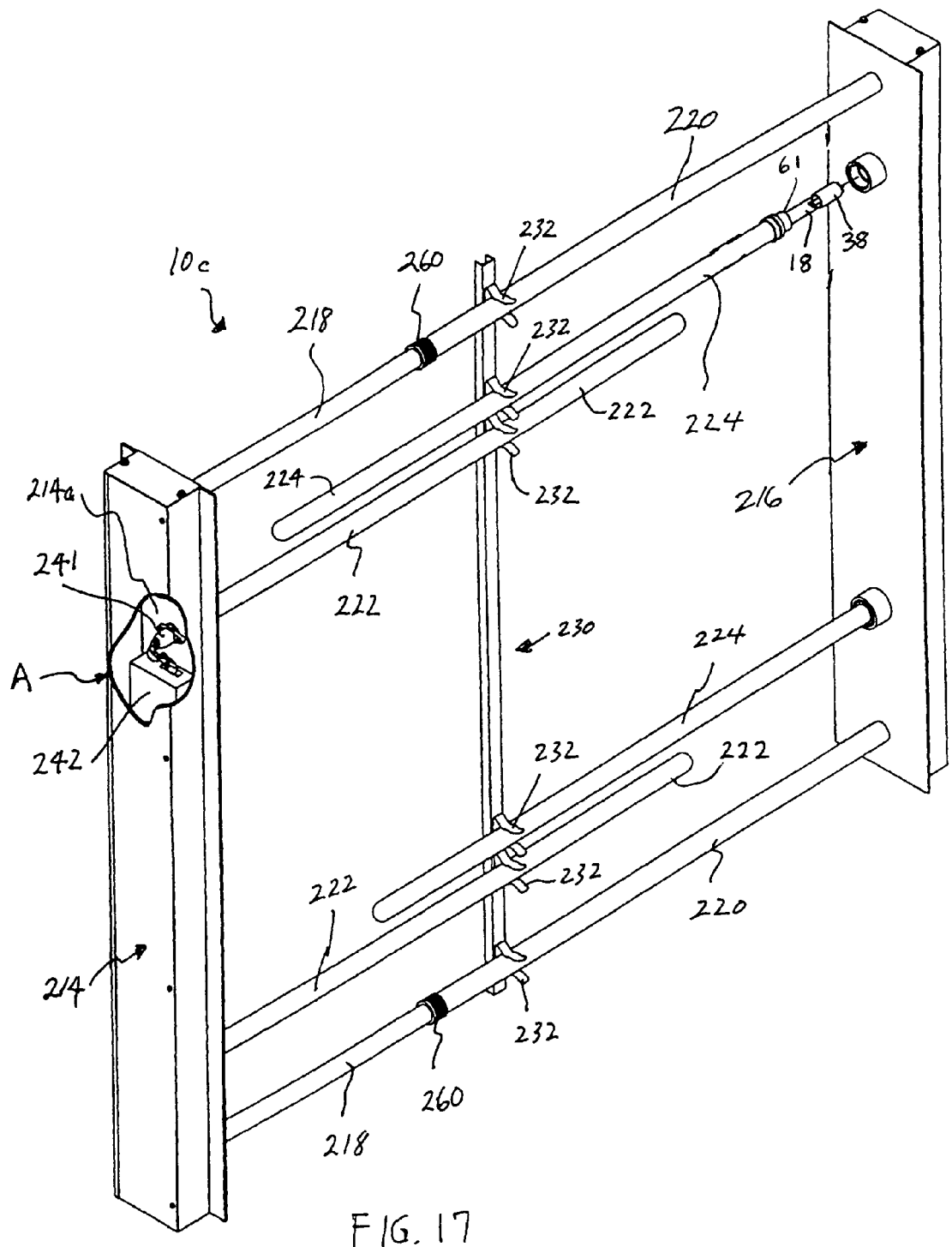
FIG. 17 is an isometric perspective view of an air disinfection module in accordance with a further embodiment of the invention.

FIG. 17 illustrates another embodiment of a fluid disinfection module in accordance with the invention herein. FIG. 17 shows module 10c which is a modification of module 10 shown in FIG. 1. Module 10c includes a first housing 214 and a second housing 216. FIG. 17 shows a pair cooperating elongate support members 218,220, preferably of tubular construction, at the upper-shown part of the module and another pair 218,220 at the bottom-shown part of the module. In each pair of elongate support members 218,220, member 218 is slidably engaged with member 220 for varying the lateral distance between first and second housings 214 and 216, respectively. Radiation permeable protective sleeves 222, preferably of a cylindrically fused quartz construction, extend from first housing 214 toward second housing 216, while protective sleeves 224 having the same construction extend from second housing 216 towards first housing 214. Protective sleeves 222 and 224 encase radiation sources in the form of elongate tubular UV lamp 18 for the same purpose as protective sleeves 60 illustrated in FIG. 1. To add rigidity and structural integrity to module 10*c*, a cross support member 230 is retained onto one of tubular support members 218,220 at the upper-shown part of the module and to one of such tubular support members at the bottom-shown part of the module.

It will be understood that more than two pairs of tubular support members 218,220 in module 10*c* can be utilized for varying the lateral distance between housings 214,216. Support members of other configurations which accomplish the same purpose can also be utilized interchangeably. Further, the number of radiation sources (e.g., UV lamp 18) with associated radiation pervious protective sleeves 222,224 can be varied to meet the needs for effective germicidal treatment of a fluid, typically air, passing through a HVAC system. It will also be understood that module 10*c* can be combined with other modules of identical or similar construction in the manner described herein and illustrated in FIGS. 15-16.

Various parts of module 10*c* of FIG. 17 are described below in greater detail to explain enhancements of this embodiment.

Figure 18:
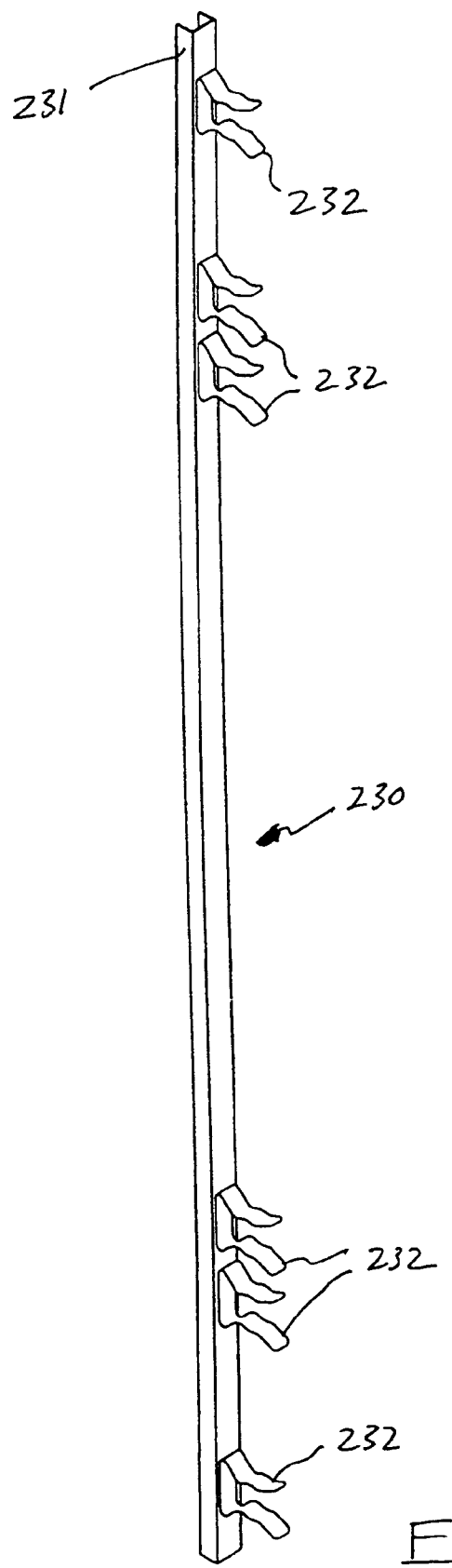
FIG. 18 is an isometric perspective view of cross support member 230 illustrated in FIG. 17.

FIG. 18 illustrates cross support member 230 which includes an elongate body 231 whose construction is that of an elongate metal channel. Body 231, as shown in FIG. 18, is preferably substantially straight from one end to the other. Cross sections other than a channel can be used, particularly those that include an angle for providing rigidity to the cross support member and which will accommodate the placement of spring clips 232 thereon.

Spring clips 232, formed of a resilient metal, are secured to elongate body 231 by any fastening means, e.g., by welding directly to body 231 (see FIG. 17) or if detachable and/or adjustable securement is desired, then with machine screws or a nut and bolt arrangement inserted through appropriate openings (not shown) in the spring clip and body 231. It will be appreciated that the placement of the spring clips along the length of body 231 will accommodate their engagement with tubular support members 218,220 and protective sleeves 222, 224. Accordingly, means may be provided for allowing spring clips 232 to be slidably engaged with body 231, e.g., by providing one or more elongate slots (not shown) along the length of body 231, to adjust the positioning of the spring clips to the body relative to tubular support members 218,220 and protective sleeves 222,224. If desired, spring clips 232 may be provided with rubber or other cushioning means on the surfaces which interface with protective sleeves 222 and 224 (FIG. 17). Spring clips 232 are especially preferred for their retaining function and ease of use., but other retaining means can also be used, such as will be apparent to those of ordinary skill in the art based on the disclosures of the specification herein. As an alternative to the cross support member 230 illustrated in FIGS. 17 and 18, the protective sleeves can be supported between tubular support members 218,220 by a wire pulled taught between the support members. The wire (not shown) can include annular receptacles (not shown) in the form of, for example, washers in spaced-apart relationship to each other for slidably receiving the protective sleeves therethrough. In this arrangement, the protective sleeves will be detachably secured within the annular receptacles. Other variations of cross support member 230 will be apparent to those of ordinary skill in the art based on the present specification.

FIG. 19 shows an annular lamp assembly receptacle 238 for receiving and detachably retaining a lamp assembly comprised of protective sleeve 224 and UV lamp 18 (see FIG. 17). FIG. 19 also shows an annular sleeve retention member 239 for receiving and detachably retaining the open end 61 (FIG. 2) of protective sleeve 224. Receptacle 238 and retention member 239 cooperate with each other as described below. Retention member 239 is of an annular configuration for mounting to the open end of protective sleeve 224. The retention member 239 is preferably fixed to the sleeve by means of an adhesive fixative, such as an epoxy glue, e.g., an ultraviolet light curing epoxy adhesive available from Norland Products, Inc. under the trade name of Norland Electronic Adhesive NEA 121. The adhesive is applied to the outer surface of the sleeve and thereafter inserted into retention member 239. As shown in greater detail in FIG. 19B, annular sleeve retention member 239 includes a first annulus 248 and a concentric second annulus 249. First annulus 248 is sized and configured to slidably receive therethrough UV lamp 18. Retention member 239 also includes a second annulus 249 sized and configured with first annulus 248 for defining an interior platform 250 for limiting the protective sleeve's penetration into member 239 when in an assembled state. Retention member 239 also includes a groove 252 on its exterior surface for receiving a resilient O-ring 253. O-ring 253 and groove 252 is sized such that O-ring 253 is positioned therein with a resistance fit.

Referring now to FIG. 19A, annular lamp assembly receptacle 238 also includes a first annulus 243 and a concentric second annulus 244. First annulus 243 is sized and configured to slidably receive therethrough lamp base 38 of UV lamp 18 (see FIGS. 2, 3 and 17). Second annulus 244 is sized and configured with first annulus 243 for defining an interior platform 246 which limits the slidable penetration of annular sleeve retention member 239 into lamp assembly receptacle 238 when both the retention member and receptacle are in their assembled state.

In similar fashion to electrical socket 74 illustrated in FIGS. 4 and 6, FIG. 19 also illustrates an electrical receptacle 241 for receiving the electrical pins 48,50 of UV lamp 18 (see FIGS. 2, 3 and 17). Electrical receptacle 241 and lamp assembly receptacle 238 are positioned on opposite sides of wall 214*a* of housing 214. Electrical receptacle 241 also includes lead wires for electrical connection with a power supply 242 in the same manner as that illustrated in FIG. 6.

Assembly of electrical socket 241, lamp assembly receptacle 238, sleeve retention member 239, and the lamp assembly with housing 214 is as follows.

Referring to FIG. 19, in a preferred construction, electrical receptacle 241 is secured to the oppositely disposed lamp assembly receptacle 238 on either side of wall 214*a* of housing 214 with fastening means 255, which according to FIG. 19, are preferably in the form of threaded machine screws or bolts. Fastening means 255 are engaged with correspondingly threaded openings 257 in lamp assembly receptacle 238, via openings 258 in electrical receptacle 241 and openings 259 provided in the wall 214*a* of housing 214 from which the lamp assembly projects. Either one or both of openings 258 and 259 may also be threaded to accommodate threaded engagement with fastening means 255. In order to align lamp assembly receptacle 238 with electrical receptacle 241, sleeve retention member 238 may include an axially extending annulus 240 for slidable engagement with opening 261 provided in wall 214a of housing 214. Preferably, opening 261 is only slightly larger than annulus 240 in order to facilitate alignment of openings 257 in lamp assembly receptacle 238 with the openings 259 in wall 214a of housing 214.

Once electrical receptacle 241 and lamp assembly receptacle 238 are secured to wall 214a of housing 214, the base 38 of UV lamp 18 is slid through receptacle 238 for engaging the electrical pins 48,50 of base 38 (see FIGS. 2, 3 and 17) with electrical receptacle 241. After retention member 239 is secured about the open end 61 of protective sleeve 224, O-ring 253 is slid over the sleeve retention member and inserted in groove 252 (FIG. 19B). As shown in FIGS. 17 and 19, the sleeve retention member 239, with the protective sleeve attached thereto, is then slid into annulus 244 (FIG. 19A) of lamp assembly receptacle 238 until the end 239a of the sleeve retention member butts against and seats with platform 246 of lamp assembly receptacle 238. As a result, O-ring 253 will be slidably and detachably engaged with the interior surface of annulus 244 of receptacle 238 with a resistance fit caused by the resulting compression of the O-ring. It will be appreciated that the remainder of the lamp assemblies in module 10c may be connected to their respective housings in similar fashion.

Figure 20:
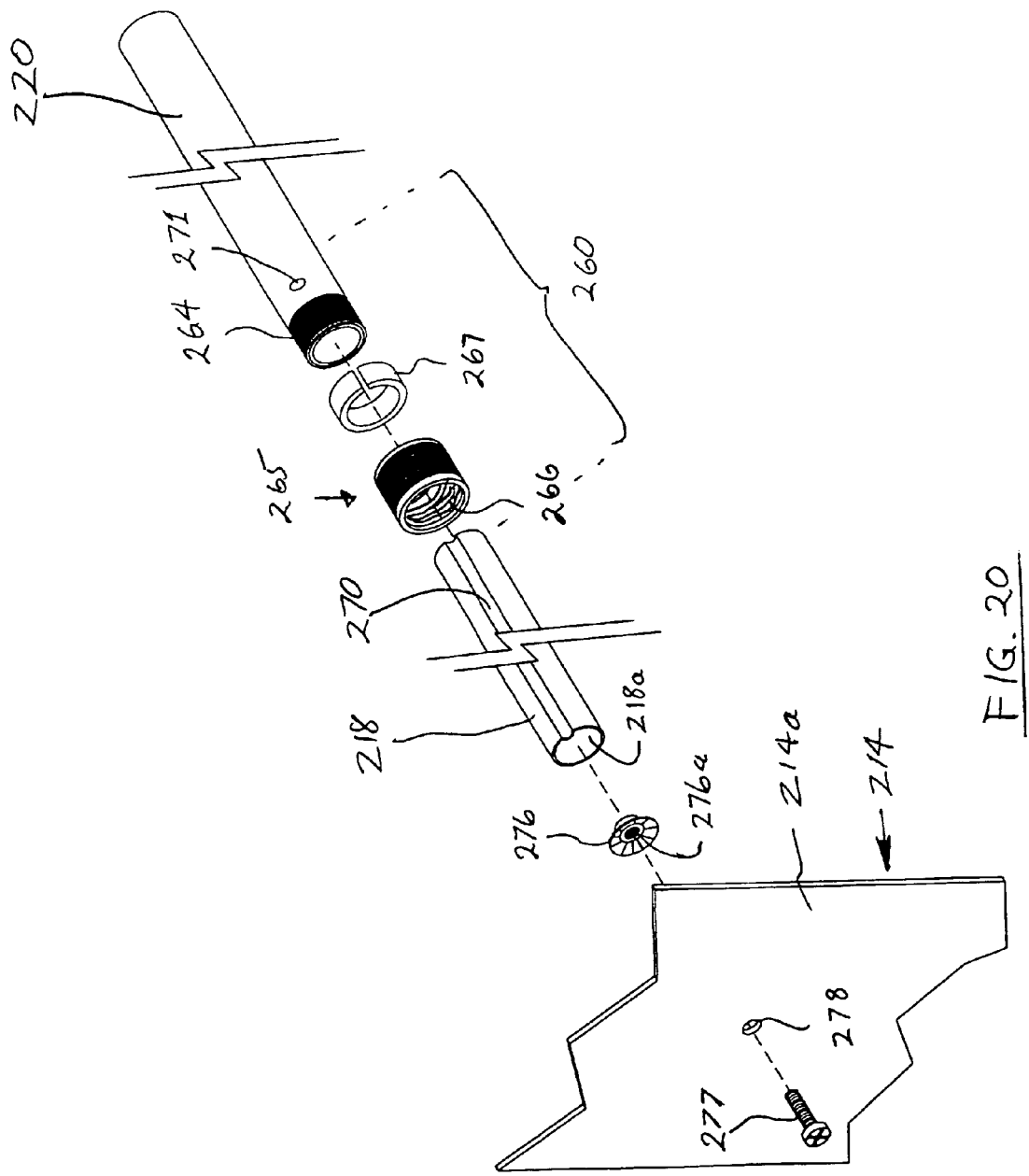
FIG. 20 is an exploded and fragmentary isometric perspective detail of a segment of FIG. 17 showing the manner of engagement of elongate support members 218,220 with each other and with housing 214.

FIG. 20 shows a preferred locking mechanism 260 for interconnecting and securing to each other the elongate support members 218 and 220 illustrated in FIG. 17. FIG. 20 also illustrates a preferred manner for the securement of elongate support member 218 to housing 214. This same manner of securement is also used to secure elongate support member 220 to housing 216.

Referring to FIG. 20, locking mechanism 260 includes an externally threaded portion 264 disposed about the end of elongate support member 220 for engaging a correspondingly threaded annular compression nut 265 with internal threads 266. Locking mechanism 260 also includes a compression ring 267 slidably engaged with elongate support member 218 which may have a resilient plastic construction as shown, or a rubber or elastomer O-ring construction. Compression ring 267 is compressed inwardly by compression nut 265 onto support member 218 when compression nut 265 is engaged with threaded portion 264 and tightened in order to detachably secure support member 218 to support member 220. The manner of engagement and securement of support member 218 with support member 220 is the same for the pair that are illustrated in FIG. 17.

The penetration of elongate support member 218 into elongate support member 220 can be readily varied by loosening compression nut 265, changing the degree of penetration, and re-tightening compression nut 265. In this way, the distance between the first and second housings 214,216 is easily adjusted for accommodating the dimensional widths of the receiving space of HVAC systems within which the apparatus is to be deployed.

Figure 20B:
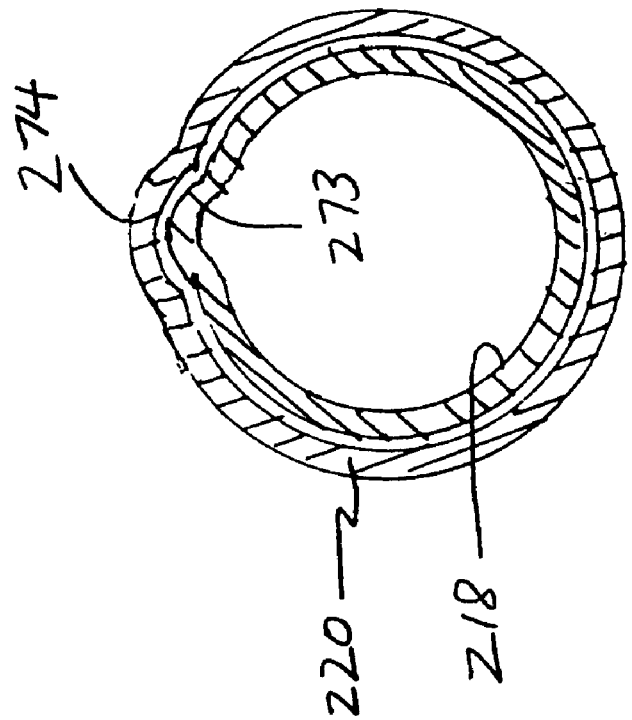
FIG. 20B is an alternative arrangement of elongate support members 218,220 shown in FIG. 20A.
Figure 20A:
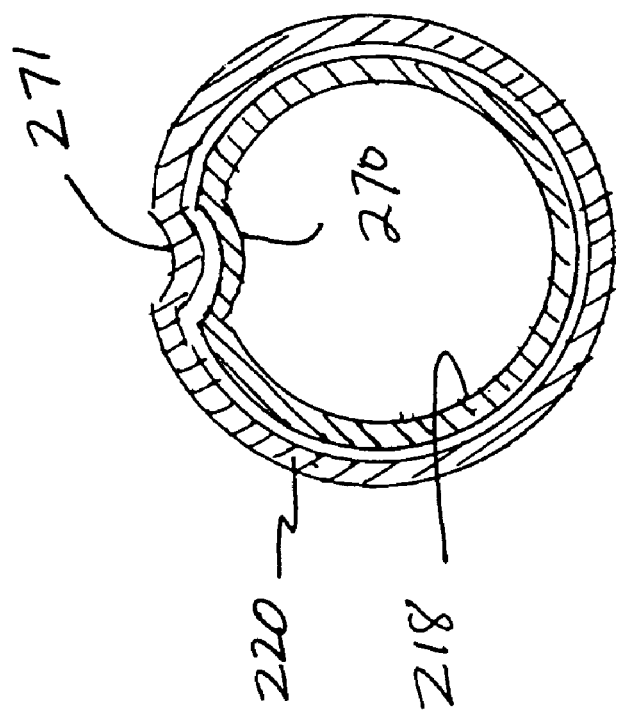
FIG. 20A is cross-sectional view of elongate support members 218,220 shown in FIG. 20 when engaged with each other.

Referring once again to FIG. 20, in order to lend additional rigidity to the modular framework defined by housings 214, 216 and support members 218,220, support member 218 is provided with a longitudinal and axially disposed channel 270 for engaging an axially disposed protrusion 271 in support member 220. As illustrated in FIG. 20, the protrusion 271 is in the form of an interiorly protruding dimple, although as shown in FIGS. 20A, 20B, protrusions 271,273 can extend along the partial or total length of support member 220. When support members 218 are inserted into corresponding support members 220, channel 270 will slidably receive protrusion 271. This arrangement has several advantages in that the substantial rotation of support member 220 relative to support member 218 is avoided thereby preventing the rotational displacement of housing 214 relative to housing 216. Also, by providing the channel/protrusion arrangement for the tubular support members, a "key" is provided to facilitate the insertion of support member 218 into support member 220.

An alternative embodiment for the channel/protrusion arrangement is illustrated in FIG. 20B where channel 274 in support member 220 is disposed on its interior surface along the partial or complete longitudinal length thereof, and protrusion 273 is partially or completely disposed along a cooperating exterior surface of support member 218. It will be understood that in accordance with the invention, other configurations for engaging support members 218,220 with each other may be utilized. For example, the partial or complete length of support members 218,220 may have a square, rectangular and/or other polygonal cross section with one member fitting within the other. This may be accompanied by appropriate locking devices for detachably securing the members to each other. An advantage of utilizing a cylindrically tubular configuration for the support members is its capability of employing locking mechanism 260 which takes the form of a compression fitting.

Support members 218,220 are preferably mounted substantially perpendicular to their respective housings 214,216. FIG. 20 additionally illustrates a preferred means for their mounting, and shows a retaining member 276 for mounting elongated support member 218 to wall 214a of housing 214. Identical or similar means may be used for mounting the other support members to their respective housings, e.g., support member 220 to corresponding wall 216a of housing 216 (see FIG. 17).

Retaining member 276 takes the form a cylindrically shaped bracket structure for containing a concentrically positioned receiving member 276a. Receiving member 276a is threaded for mateably receiving a correspondingly threaded member 277, e.g., a threaded machine bolt or screw, through an opening 278 provided in wall 214a of housing 214 for that purpose. As shown in FIG. 20, retaining member 276 is of a stiff, resilient, metal construction, e.g., stainless steel, for slidable engagement with the interior opening 218a of support member 218. The resilience of member 276 is in the radially expandable direction and is such that its engagement with opening 218a is with a high resistance fit. The resistance fit of retaining member 276 with the interior of support member 218 will be sufficient to provide a rigid and secure attachment of support member 218 to wall 214a of housing 214 when threaded member 277 is securely engaged with receiving member 276a.

The above-described ultraviolet light modules or arrays thereof may be installed in a variety locations in a HVAC system depending on access thereto, preferably before or after the evaporator coils of the system's air conditioning unit(s). In addition, the modules or arrays may be stacked or placed in a series-type arrangement within the HVAC system for treating the air passing therethrough.

The apparatus and module according to the invention herein also has application to systems other than the treatment of air. It may be used, for example, for the treatment of a fluid that includes wastewater or potable water passing through a conduit, provided that the necessary precautions are taken for water proofing the housings to protect the electronics contained therein and using protective sleeves for insulating the UV lamps from moisture.

Since other modifications and changes may be varied to fit the particular operating requirements and environments of the invention, which will be apparent to those skilled in the art, the invention is not considered to be limited to the embodiments chosen for purposes of disclosure, and covers all changes and modifications which do not constitute departures from the true spirit and scope thereof.

What is claimed is:

1. An air disinfection module for use in a HVAC system comprising a first housing and a second housing, each of said housings comprising at least one support member joined with the other for defining an adjustable, framework structure for adjusting said housings in laterally spaced-apart relationship to each other, each of said housings further comprising (i) a lamp assembly comprising at least one ultraviolet radiation source communicating with and projecting from its respective housing towards its opposite housing, and a radiation pervious protective sleeve disposed about each radiation source; (ii) electric transmission means communicating with said ultraviolet radiation sources and with at least one source of electrical power for supplying electricity to said ultraviolet radiation source; and (iii) at least one cross support member communicating with said protective sleeves and said support members for supporting said sleeves and their corresponding ultraviolet radiation sources between said housings.

2. An air disinfection module, comprising
(a) a first housing and a second housing;
(b) means defining an interconnecting adjustable framework structure for maintaining said housings in adjustable, spaced-apart relationship to each other;
(c) means defining one or more ultraviolet radiation sources communicating with and projecting from each housing towards the other housing;
(d) a radiation pervious protective sleeve disposed about each radiation source;
(e) electric transmission means communicating with said ultraviolet radiation sources and at least one source of electrical power for powering said ultraviolet radiation sources; and
(f) means communicating with said protective sleeves and said adjustable framework structure for supporting said sleeves and their corresponding ultraviolet radiation sources between said housings.

3. An air disinfection module comprising a first housing and a second housing, each of said housings comprising at least one support member disposed about each end of said housings and joined with the respective support member of the other housing for defining a framework structure for varying the lateral distance between said housings, each of said housings further comprising (a) at least one lamp assembly comprising one or more ultraviolet radiation sources communicating with and projecting from its respective housing towards the other housing, and a radiation pervious protective sleeve disposed about each radiation source; (b) at least one ballast for supplying electricity to said ultraviolet radiation sources; and (c) at least one cross support member communicating with said protective sleeves and said support members for supporting said sleeves and their corresponding ultraviolet radiation sources between said housings.

4. An air disinfection module comprising
(a) a first housing and a second housing, said housings being arranged in laterally spaced-apart relationship to each other, each housing comprising a plurality of elongate support members extending laterally therefrom for slidable engagement with the corresponding elongate support members of the other housing for varying the distance between said first and second housings, said first housing, second housing and corresponding elongate support members defining an interconnecting framework structure for supporting a plurality of lamp assemblies
  (i) that are detachably mounted to each of said housings,
  (ii) that project laterally from their corresponding housing towards the other housing, and
  (iii) that communicate with one or more ballasts disposed within or without their respective housing;
each lamp assembly comprising an elongate ultraviolet lamp provided with a lamp base disposed at one end thereof and electrical terminal pins mounted to said lamp base, and a radiation pervious protective sleeve, open at least at one end thereof, disposed about each ultraviolet lamp;
(b) at least one cross support member communicating with said protective sleeves and said support members for supporting said lamp assemblies between said housings; and
(c) an annular lamp assembly receptacle disposed about an opening provided in a surface of the housing from which the ultraviolet lamp projects, said annular lamp assembly receptacle comprising a first and second annulus, the first annulus being sized and configured for receiving therethrough the lamp base of said ultraviolet lamp, and the second annulus being sized and configured with the first annulus for defining an interior platform for limiting penetration of the slidable receipt within said lamp assembly receptacle of an annular sleeve retention member disposed about the open end of said protective sleeve.

5. The module according to claims 1, 3 or 4 wherein said cross support member is detachably secured to said protective sleeves and said support members.

6. The module according to claim 5 wherein said cross support member comprises retention means communicating with an elongate rigid member, said retention means being configured for detachable securement to said protective sleeves and said support members.

7. The module according to claim 6 wherein the retention means are of a resilient construction.

8. The module according to claim 7 wherein the retention means comprises a plurality of spring clips in fixed or detachably fixed relationship with said elongate rigid member for corresponding engagement with said protective sleeves and said support members.

9. The module according to claims 1 or 3 wherein said ultraviolet radiation source is an ultraviolet lamp of an elongate tubular construction that includes a lamp base disposed at one end thereof and electrical terminal pins mounted to said lamp base, and the radiation pervious protective sleeve is of a cylindrical fused quartz construction that is open at one end thereof and closed at its opposite end.

10. The module according to claim 9 additionally comprising an annular lamp assembly receptacle disposed about an opening provided in a surface of the housing from which the ultraviolet lamp projects, said annular lamp assembly receptacle comprising a first and second annulus, the first annulus being sized and configured for receiving therethrough the lamp base of said ultraviolet lamp, and the second annulus being sized and configured with the first annulus for defining an interior platform for limiting penetration of the slidable receipt within said lamp assembly receptacle of an annular sleeve retention member disposed about the open end of said protective sleeve.

11. The module according to claims 4 or 10 wherein the annular sleeve retention member is fixed about the open end of said protective sleeve.

12. The module according to claims 4 or 10 wherein the annular sleeve retention member is detachably secured to the annular lamp assembly receptacle with a resistance fit.

13. The module according to claim 12 wherein the resistance fit is achieved by a resilient O-ring disposed about the outer surface of the annulus of said annular sleeve retention member.

14. The module according to claims 4 or 10 wherein the annular lamp assembly receptacle is secured to an electrical receptacle configured for receiving the electrical pins of said lamp base, said electrical receptacle being disposed on the opposite side of the housing surface about the opening therein.

15. The module according to claim 14 wherein the annular lamp assembly receptacle, electrical receptacle and housing surface comprise corresponding openings to receive means for their securement to each other.

16. The module according to claim 15 wherein said means comprises fastening means.

17. The module according to claim 16 wherein the corresponding openings of said lamp assembly receptacle are threaded for engaging a correspondingly threaded fastening means.

18. The module according to claim 17 wherein the fastening means comprises a threaded bolt or screw.

19. The module according to claims 1 or 3 wherein said support member is slidably engaged with the other for varying the lateral distance between said first and second housings.

20. The module according to claim 4 or 19 wherein one end of said elongate support member is disposed about each end of each of said housings.

21. The module according to claims 4 or 20 wherein the elongate support member is of a tubular construction.

22. The module according to claims 4 or 20 wherein the elongate support member is of a cylindrical tubular construction.

23. The module according to claim 22 wherein the tubular support member includes a retaining member configured for engagement within one end of said tubular support member, said retaining member comprising a receptacle for receiving a fastening member through an opening provided in a surface of the housing from which the tubular support member projects for detachably securing said tubular support member to its respective housing.

24. The module according to claim 23 wherein the retaining member is in the form of a cylindrically configured bracket structure that resiliently expands into the end of its associated elongate support member.

25. The module according to claim 24 wherein the cylindrically configured bracket structure is slidably engaged with the interior of the tubular support member with a resistance fit.

26. The module according to claim 23 wherein the receptacle and fastening member are threaded for threaded engagement with each other.

27. The module according to claim 22 wherein the tubular support member of said first housing is slidably engaged and mated with the tubular support member of said second housing, the tubular support members of said first and second housings being detachably secured to each other by a locking mechanism.

28. The module according to claim 27 wherein the surface of the tubular support member of said first housing defines a longitudinal and axially disposed channel for slidably receiving a protrusion disposed on the surface of the tubular support member of said second housing for mateable engagement of said protrusion and channel when the tubular support members are slidably engaged with each other.

29. The module according to claim 28 wherein the channel is disposed on the interior surface of the tubular support member of said first housing and the protrusion is disposed on the exterior surface of the tubular support member of said second housing.

30. The module according to claim 28 wherein the channel is disposed on the exterior surface of the tubular support member of said first housing and the protrusion is disposed on the interior surface of the tubular support member of said second housing.

31. The module according to claim 27 wherein the locking mechanism comprises a compression fitting.

32. The module according to claim 31 wherein the compression fitting comprises an interiorly threaded cylindrical annulus for slidable engagement with the tubular support member of said first housing and engagement with a correspondingly threaded end portion of the tubular support member of said second housing, and a corresponding compression ring for slidable engagement with the tubular support member of said first housing.

33. The module according to claim 14 wherein the electrical receptacle is connected to at least one ballast for supplying electricity to said lamp.

34. The module according to claims 1, 3 or 4 wherein each housing comprises a plurality of lamp assemblies.

35. The module according to claim 34 wherein each housing comprises a plurality of ballasts for supplying electricity to said lamp assemblies.

* * * * *